(12) United States Patent
Herrmann et al.

(10) Patent No.: US 7,396,911 B2
(45) Date of Patent: *Jul. 8, 2008

(54) CHIMERIC POLYPEPTIDES CONTAINING CHEMOKINE DOMAINS

(75) Inventors: Stephen H. Herrmann, Wellesley, MA (US); Stephen L. Swanberg, Boston, MA (US)

(73) Assignee: Genetics Institute, LLC, Cambridge, MA (US)

( * ) Notice: Subject to any disclaimer, the term of this patent is extended or adjusted under 35 U.S.C. 154(b) by 500 days.

This patent is subject to a terminal disclaimer.

(21) Appl. No.: 10/614,475

(22) Filed: Jul. 7, 2003

(65) Prior Publication Data

US 2007/0160570 A1    Jul. 12, 2007

Related U.S. Application Data

(60) Continuation of application No. 09/467,638, filed on Dec. 20, 1999, now Pat. No. 6,730,296, which is a division of application No. 08/808,720, filed on Feb. 28, 1997, now Pat. No. 6,100,387.

(51) Int. Cl.
*C07K 14/00* (2006.01)

(52) U.S. Cl. ............... 530/351; 530/350; 530/387.1; 530/388.23; 435/70.1

(58) Field of Classification Search ............ 536/23.4, 536/23.5, 252.3, 325; 435/69.1, 252.3, 325, 435/172.3, 320.1, 70.1; 424/133.1; 530/350, 530/387.3, 351, 388.23
See application file for complete search history.

(56) References Cited

U.S. PATENT DOCUMENTS

| | | | |
|---|---|---|---|
| 4,235,871 A | 11/1980 | Papahandjopoulos et al. | |
| 4,501,728 A | 2/1985 | Geho et al. | |
| 4,518,584 A | 5/1985 | Mark et al. | |
| 4,737,323 A | 4/1988 | Martin et al. | |
| 4,837,028 A | 6/1989 | Allen | |
| 5,270,181 A | 12/1993 | McCoy et al. | |
| 5,292,646 A | 3/1994 | McCoy et al. | |
| 5,563,048 A | 10/1996 | Honjo et al. | |
| 5,580,754 A | 12/1996 | Samal | |
| 5,605,817 A | 2/1997 | Coleman et al. | |
| 5,616,688 A | 4/1997 | Cerami et al. | |
| 5,650,150 A | 7/1997 | Gillies | |
| 6,730,296 B1 * | 5/2004 | Herrmann et al. ......... | 424/85.1 |

FOREIGN PATENT DOCUMENTS

| | | |
|---|---|---|
| EP | 0 699 766 A | 3/1996 |
| EP | 0 763 543 A2 | 3/1997 |
| EP | 0 816 510 A1 | 1/1998 |
| WO | WO 95/21258 | 8/1995 |
| WO | WO 96/04388 | 2/1996 |
| WO | WO 96/13587 | 5/1996 |
| WO | WO 96/17935 | 6/1996 |
| WO | WO 96/23888 A | 8/1996 |
| WO | WO 96/34819 | 11/1996 |
| WO | WO 96/38559 | 12/1996 |
| WO | WO 96/39520 | 12/1996 |
| WO | WO 96/39521 | 12/1996 |
| WO | WO 96/39522 | 12/1996 |
| WO | WO 96/40762 | 12/1996 |
| WO | WO 96/40786 | 12/1996 |
| WO | WO 97/00691 | 1/1997 |
| WO | WO 97/19173 | 5/1997 |
| WO | WO 97/34631 A1 | 9/1997 |
| WO | WO 94/29341 | 12/1997 |
| WO | WO 98/04698 A1 | 2/1998 |

OTHER PUBLICATIONS

U.S. Appl. No. 08/165,301, filed Dec. 10, 1993, McCoy and LaVallie.
U.S. Appl. No. 08/535,116, filed Oct. 11, 1995.
U.S. Appl. No. 08/595,590, filed Feb. 2, 1996, Gray et al.
U.S. Appl. No. 08/810,436, filed Mar. 4, 1997, McCoy and LaVallie.
Kaufman et al., Nucleic Acids Res 19:4485-4490 (1991).
Kaufman, Methods in Enzmology 185:537-566 (1990).
Current Protocols in Immunology, Ed. by J.E. Coligan, A.M. Kruisbeek, D. H. Margulier, E.M. Shevach, W. Strober, Pub. by Green Publishing Associates and Wiley-Interscience (Chapter 6.12, Measurement of alpha and beta Chemokines 6.12.1-6.12.28), 1995.
Baub et al. J. Clin. Invest. 95:1370-1376, 1995.
Lind et al. APMIS 103:140-146, 1995.
Muller et al. Eur. J. Immunol. 25:1744-1748, 1995.
Gruber et al. J. of Immunol. 153: 1762-1768, 1994.
Johnston et al.. J. of Immunol. 153.1762-1768. 1994.
Saragovi et al. Bio/Technology 10, 773-778 (1992).
McDowell, et al. J. Amer. Chem Soc. 114 9245-9253 (1992).
Current Protocols in Immunology, edited by J.E. Coligan, A.M. Kruisbeck, D. H. Margulier, E.M. Shevach, W. Strober, Pub. by Green Publishing Associates and Wiley-Interscience (Chapter 7.28. Measurement of Cellular Adhesion under static conditions 7 28.1-7. 28 22), 1995.
Takai et al. Proc. Natl Acad. Sci. USA 84.6864-6868.1987.
Bierer et al. J. Exp. Med 168:1145-1156.1988.

(Continued)

*Primary Examiner*—David J. Blanchard
*Assistant Examiner*—Parithosh K. Tungaturthi
(74) *Attorney, Agent, or Firm*—Ivor R. Elrifi; David E. Johnson; Mintz, Levin, Cohn, Ferris, Glovsky and Popeo, P.C.

(57) ABSTRACT

This invention provides a chimeric DNA molecule comprising a sequence encoding a chemokine polypeptide covalently attached to a heterologous polypeptide, the encoded chimeric polypeptide, and uses thereof.

18 Claims, 3 Drawing Sheets

OTHER PUBLICATIONS

Rosenstein et al. J. Exp. Med. 169:149-160 1989.
Stoltenbert et al. J. Immunol. Methods 175-59-68.1994.
Stitt et al. Cell 80:661-670.1995.
Merrifield, J. Amer. Chem Soc 85 2149-2154 (1963).
Krstenansky et al. REBS Lett. 211, 10 (1987).
Arenzana-Seisdedos et al. Nature 383:400 (1996).
Bates, P., Cell 86: 1-3 (1996).
Bates, C.C. et al., J. Exp. Med. 184: 1101-1109 (1996).
Cocchi, F. et al. Science 270: 1811-1815 (1995).
Dragic, T. et al., Nature 381: 667-673 (1996).
J nsson, U. et al., Bio Techniques 11:620-627 (1991).
Mackay, C. R. J. Exp. Med. 184:799-802 (1996).
Nagasawa, T. et al., nature 382:635-638 (1996).
Nagasawa, T. et al., Proc. Natl. Acad Sci. USA 91:2305-2309 (1994).
Oberlin, E. et al., Nature 382:833-835 (1996).
Schmidtmayerova, H. et al., Nature 382:767 (1996).
Seachrist, L., BioWorld Today 8 (23): 1,4 (1997).
Tashiro K. et al. Science 261: 600-603 (1993).
Wells, T.N.C. et al., Annals of the New York academy of Sciences, 796: 245-246 (1996).
Wu, L. et al., Nature 384: 179-183 (1996).
Howard et al., Trends in Biochemistry 14: 46-51, Feb. 1996.

* cited by examiner

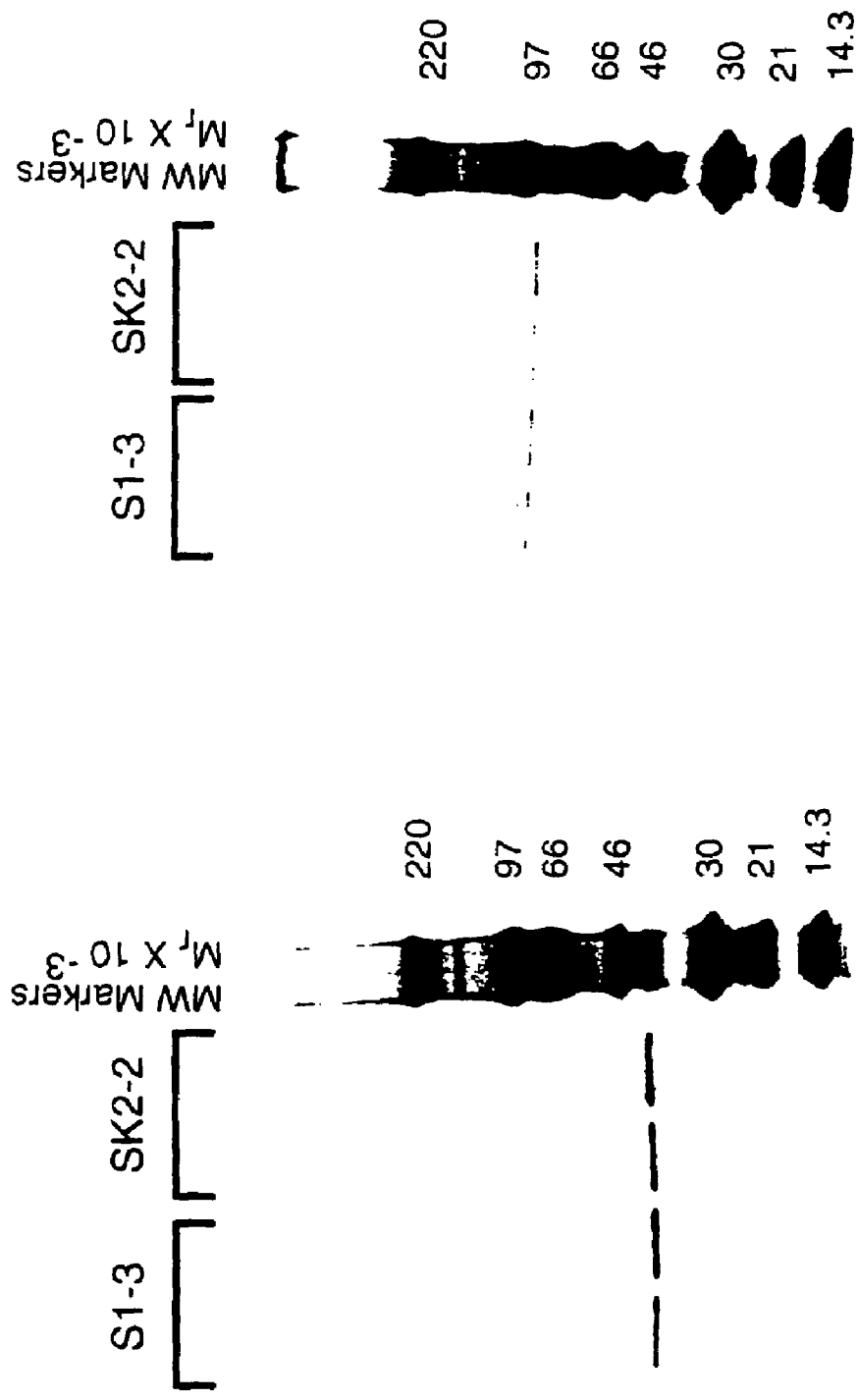

Figure 1D Non-Reduced MIP-FC
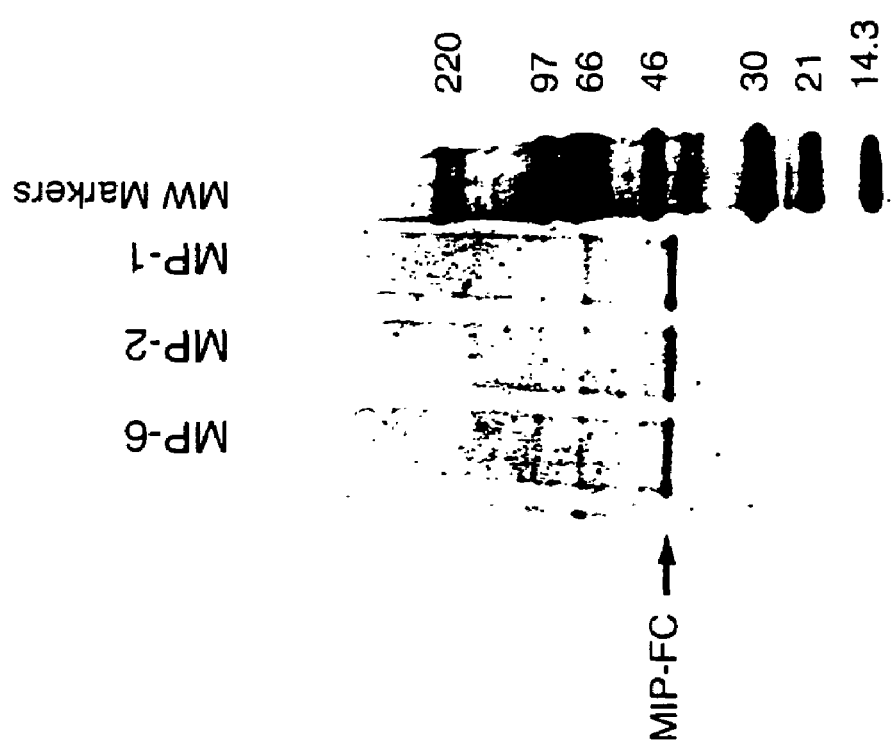
Figure 1C Reduced MIP-FC

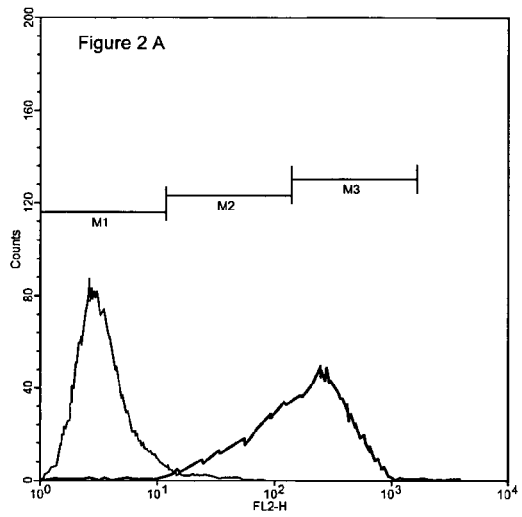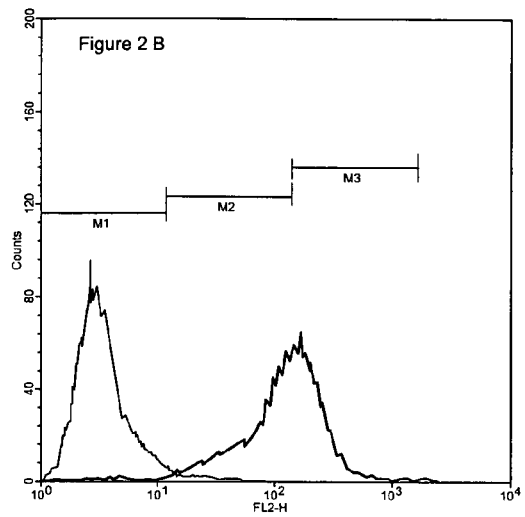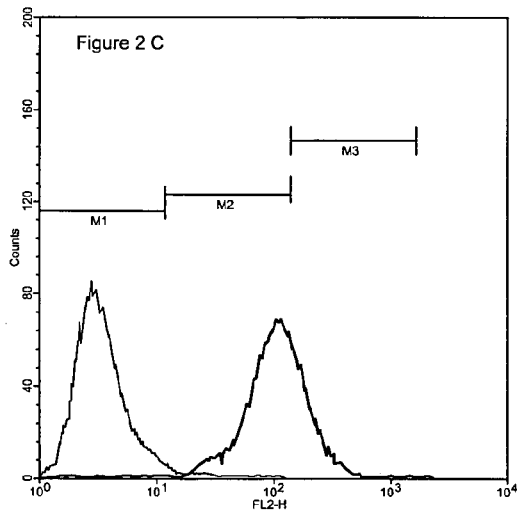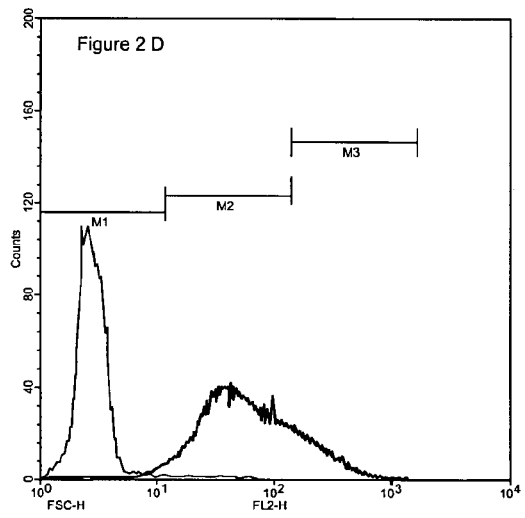

SEQUENCE LISTING (1) GENERAL INFORMATION:

(iii) NUMBER OF SEQUENCES: 10

(2) INFORMATION FOR SEQ ID NO: 1:

(i) SEQUENCE CHARACTERISTICS:
      (A) LENGTH: 328 amino acids
      (B) TYPE: amino acid
      (C) STRANDEDNESS: <Unknown>
      (D) TOPOLOGY: linear (ii) MOLECULE TYPE: protein (xi) SEQUENCE DESCRIPTION: SEQ ID NO: 1:

```
Met Asn Ala Lys Val Val Val Leu Val Leu Val Leu Thr Ala Leu
1               5                   10                  15

Cys Leu Ser Asp Gly Lys Pro Val Ser Leu Ser Tyr Arg Cys Pro Cys
                20                  25                  30

Arg Phe Phe Glu Ser His Val Ala Arg Ala Asn Val Lys His Leu Lys
                35                  40                  45

Ile Leu Asn Thr Pro Asn Cys Ala Leu Gln Ile Val Ala Arg Leu Lys
            50                  55                  60

Asn Asn Asn Arg Gln Val Cys Ile Asp Pro Lys Leu Lys Trp Ile Gln
65                  70                  75                  80

Glu Tyr Leu Glu Lys Ala Leu Asn Lys Gly Ser Gly Ser Gly Ser Gly
                85                  90                  95

Ser Gly Ser Glu Ser Lys Tyr Gly Pro Pro Cys Pro Ser Cys Pro Ala
                100                 105                 110

Pro Glu Phe Glu Gly Ala Pro Ser Val Phe Leu Phe Pro Pro Lys Pro
                115                 120                 125

Lys Asp Thr Leu Met Ile Ser Arg Thr Pro Glu Val Thr Cys Val Val
            130                 135                 140

Val Asp Val Ser Gln Glu Asp Pro Glu Val Gln Phe Asn Trp Tyr Val
145                 150                 155                 160

Asp Gly Val Glu Val His Asn Ala Lys Thr Lys Pro Arg Glu Glu Gln
                165                 170                 175

Phe Asn Ser Thr Tyr Arg Val Val Ser Val Leu Thr Val Leu His Gln
                180                 185                 190

Asp Trp Leu Asn Gly Lys Glu Tyr Lys Cys Lys Val Ser Asn Lys Gly
            195                 200                 205

Leu Pro Ser Ser Ile Glu Lys Thr Ile Ser Lys Ala Lys Gly Gln Pro
            210                 215                 220

Arg Glu Pro Gln Val Tyr Thr Leu Pro Pro Ser Gln Glu Glu Met Thr
225                 230                 235                 240

Lys Asn Gln Val Ser Leu Thr Cys Leu Val Lys Gly Phe Tyr Pro Ser
                245                 250                 255

Asp Ile Ala Val Glu Trp Glu Ser Asn Gly Gln Pro Glu Asn Asn Tyr
                260                 265                 270

Lys Thr Thr Pro Pro Val Leu Asp Ser Asp Gly Ser Phe Phe Leu Tyr
            275                 280                 285
```

```
Ser Arg Leu Thr Val Asp Lys Ser Arg Trp Gln Glu Gly Asn Val Phe
    290                 295                 300

Ser Cys Ser Val Met His Glu Ala Leu His Asn His Tyr Thr Gln Lys
305                 310                 315                 320

Ser Leu Ser Leu Ser Leu Gly Lys
                325
```

(2) INFORMATION FOR SEQ ID NO: 2:

(i) SEQUENCE CHARACTERISTICS:
        (A) LENGTH: 1222 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO: 2:

```
GCGGCCGCGC CATGAACGCC AAGGTCGTGG TCGTGCTGGT CCTCGTGCTG ACCGCGCTCT      60

GCCTCAGCGA CGGGAAGCCC GTCAGCCTGA GCTACAGATG CCCATGCCGA TTCTTCGAAA     120

GCCATGTTGC CAGAGCCAAC GTCAAGCATC TCAAAATTCT CAACACTCCA AACTGTGCCC     180

TTCAGATTGT AGCCCGGCTG AAGAACAACA ACAGACAAGT GTGCATTGAC CCGAAGCTAA     240

AGTGGATTCA GGAGTACCTG GAGAAAGCTT TAAACAAGGG ATCCGGCTCT GGGAGCGGCT     300

CTGGCTCTGA GTCCAAATAT GGTCCCCCAT GCCCATCATG TCCAGGTAAG CCAACCCAGG     360

CCTCGCCCTC CAGCTCAAGG CGGGACAGGT GCCCTAGAGT AGCCTGCATC CAGGGACAGG     420

CCCCAGCCGG GTGCTGACGC ATCCACCTCC ATCTCTTCCT CAGCACCTGA GTTCGAGGGG     480

GCACCATCAG TCTTCCTGTT CCCCCCAAAA CCCAAGGACA CTCTCATGAT CTCCCGGACC     540

CCTGAGGTCA CGTGCGTGGT GGTGGACGTG AGCCAGGAAG ACCCCGAGGT CCAGTTCAAC     600

TGGTACGTGG ATGGCGTGGA GGTGCATAAT GCCAAGACAA AGCCGCGGGA GGAGCAGTTC     660

AACAGCACGT ACCGTGTGGT CAGCGTCCTC ACCGTCCTGC ACCAGGACTG GCTGAACGGC     720

AAGGAGTACA AGTGCAAGGT CTCCAACAAA GGCCTCCCGT CCTCCATCGA GAAAACCATC     780

TCCAAAGCCA AGGTGGGACC CACGGGGTG CGAGGGCCAC ACGGACAGAG GTCAGCTCGG     840

CCCACCCTCT GCCCTGGGAG TGACCGCTGT GCCAACCTCT GTCCCTACAG GGCAGCCCCG     900

AGAGCCACAG GTGTACACCC TGCCCCCATC CCAGGAGGAG ATGACCAAGA ACCAGGTCAG     960

CCTGACCTGC CTGGTCAAAG GCTTCTACCC CAGCGACATC GCCGTGGAGT GGGAGAGCAA    1020

TGGGCAGCCG GAGAACAACT ACAAGACCAC GCCTCCCGTG CTGGACTCCG ACGGCTCCTT    1080

CTTCCTCTAC AGCAGGCTAA CCGTGGACAA GAGCAGGTGG CAGGAGGGGA ATGTCTTCTC    1140

ATGCTCCGTG ATGCATGAGG CTCTGCACAA CCACTACACA CAGAAGAGCC TCTCCCTGTC    1200

TCTGGGTAAA TGATAAGAAT TC                                             1222
```

(2) INFORMATION FOR SEQ ID NO: 3:

(i) SEQUENCE CHARACTERISTICS:
        (A) LENGTH: 326 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 3:

Met Asn Ala Lys Val Val Val Val Leu Val Leu Val Leu Thr Ala Leu

```
               1               5                  10                 15
            Cys Leu Ser Lys Pro Val Ser Leu Ser Tyr Arg Cys Pro Cys Arg Phe
                            20                  25                  30

Phe Glu Ser His Val Ala Arg Ala Asn Val Lys His Leu Lys Ile Leu
                            35                  40                  45

Asn Thr Pro Asn Cys Ala Leu Gln Ile Val Ala Arg Leu Lys Asn Asn
                 50                  55                  60

Asn Arg Gln Val Cys Ile Asp Pro Lys Leu Lys Trp Ile Gln Glu Tyr
             65                  70                  75                  80

Leu Glu Lys Ala Leu Asn Lys Gly Ser Gly Ser Gly Ser Gly Ser Gly
                            85                  90                  95

Ser Glu Ser Lys Tyr Gly Pro Pro Cys Pro Ser Cys Pro Ala Pro Glu
                            100                 105                 110

Phe Glu Gly Ala Pro Ser Val Phe Leu Phe Pro Pro Lys Pro Lys Asp
                            115                 120                 125

Thr Leu Met Ile Ser Arg Thr Pro Glu Val Thr Cys Val Val Val Asp
                 130                 135                 140

Val Ser Gln Glu Asp Pro Glu Val Gln Phe Asn Trp Tyr Val Asp Gly
            145                 150                 155                 160

Val Glu Val His Asn Ala Lys Thr Lys Pro Arg Glu Glu Gln Phe Asn
                            165                 170                 175

Ser Thr Tyr Arg Val Val Ser Val Leu Thr Val Leu His Gln Asp Trp
                            180                 185                 190

Leu Asn Gly Lys Glu Tyr Lys Cys Lys Val Ser Asn Lys Gly Leu Pro
                            195                 200                 205

Ser Ser Ile Glu Lys Thr Ile Ser Lys Ala Lys Gly Gln Pro Arg Glu
                 210                 215                 220

Pro Gln Val Tyr Thr Leu Pro Pro Ser Gln Glu Met Thr Lys Asn
            225                 230                 235                 240

Gln Val Ser Leu Thr Cys Leu Val Lys Gly Phe Tyr Pro Ser Asp Ile
                            245                 250                 255

Ala Val Glu Trp Glu Ser Asn Gly Gln Pro Glu Asn Asn Tyr Lys Thr
                            260                 265                 270

Thr Pro Pro Val Leu Asp Ser Asp Gly Ser Phe Phe Leu Tyr Ser Arg
                            275                 280                 285

Leu Thr Val Asp Lys Ser Arg Trp Gln Glu Gly Asn Val Phe Ser Cys
                 290                 295                 300

Ser Val Met His Glu Ala Leu His Asn His Tyr Thr Gln Lys Ser Leu
            305                 310                 315                 320

Ser Leu Ser Leu Gly Lys
                            325

(2) INFORMATION FOR SEQ ID NO: 4:

(i) SEQUENCE CHARACTERISTICS:
                (A) LENGTH: 1216 base pairs
                (B) TYPE: nucleic acid
                (C) STRANDEDNESS: double
                (D) TOPOLOGY: linear (ii) MOLECULE TYPE: cDNA (xi) SEQUENCE DESCRIPTION: SEQ ID NO: 4:

GCGGCCGCGC CATGAACGCC AAGGTCGTGG TCGTGCTGGT CCTCGTGCTG ACCGCGCTCT          60

GCCTCAGCAA GCCCGTCAGC CTGAGCTACA GATGCCCATG CCGATTCTTC GAAAGCCATG        120
```

-continued

```
TTGCCAGAGC CAACGTCAAG CATCTCAAAA TTCTCAACAC TCCAAACTGT GCCCTTCAGA      180

TTGTAGCCCG GCTGAAGAAC AACAACAGAC AAGTGTGCAT TGACCCGAAG CTAAAGTGGA      240

TTCAGGAGTA CCTGGAGAAA GCTTTAAACA AGGGATCCGG CTCTGGGAGC GGCTCTGGCT      300

CTGAGTCCAA ATATGGTCCC CCATGCCCAT CATGTCCAGG TAAGCCAACC CAGGCCTCGC      360

CCTCCAGCTC AAGGCGGGAC AGGTGCCCTA GAGTAGCCTG CATCCAGGGA CAGGCCCCAG      420

CCGGGTGCTG ACGCATCCAC CTCCATCTCT TCCTCAGCAC CTGAGTTCGA GGGGGCACCA      480

TCAGTCTTCC TGTTCCCCCC AAAACCCAAG GACACTCTCA TGATCTCCCG GACCCCTGAG      540

GTCACGTGCG TGGTGGTGGA CGTGAGCCAG GAAGACCCCG AGGTCCAGTT CAACTGGTAC      600

GTGGATGGCG TGGAGGTGCA TAATGCCAAG ACAAAGCCGC GGGAGGAGCA GTTCAACAGC      660

ACGTACCGTG TGGTCAGCGT CCTCACCGTC CTGCACCAGG ACTGGCTGAA CGGCAAGGAG      720

TACAAGTGCA AGGTCTCCAA CAAAGGCCTC CCGTCCTCCA TCGAGAAAAC CATCTCCAAA      780

GCCAAAGGTG GGACCCACGG GGTGCGAGGG CCACACGGAC AGAGGTCAGC TCGGCCCACC      840

CTCTGCCCTG GGAGTGACCG CTGTGCCAAC CTCTGTCCCT ACAGGGCAGC CCGAGAGCC       900

ACAGGTGTAC ACCCTGCCCC CATCCCAGGA GGAGATGACC AAGAACCAGG TCAGCCTGAC      960

CTGCCTGGTC AAAGGCTTCT ACCCCAGCGA CATCGCCGTG GAGTGGGAGA GCAATGGGCA     1020

GCCGGAGAAC AACTACAAGA CCACGCCTCC CGTGCTGGAC TCCGACGGCT CCTTCTTCCT     1080

CTACAGCAGG CTAACCGTGG ACAAGAGCAG GTGGCAGGAG GGGAATGTCT TCTCATGCTC     1140

CGTGATGCAT GAGGCTCTGC ACAACCACTA CACACAGAAG AGCCTCTCCC TGTCTCTGGG     1200

TAAATGATAA GAATTC                                                     1216
```

(2) INFORMATION FOR SEQ ID NO: 5:

(i) SEQUENCE CHARACTERISTICS:
        (A) LENGTH: 331 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 5:

```
Met Gln Val Ser Thr Ala Ala Leu Ala Val Leu Leu Cys Thr Met Ala
1               5                   10                  15

Leu Cys Asn Gln Phe Ser Ala Ser Leu Ala Ala Asp Thr Pro Thr Ala
            20                  25                  30

Cys Cys Phe Ser Tyr Thr Ser Arg Gln Ile Pro Gln Asn Phe Ile Ala
        35                  40                  45

Asp Tyr Phe Glu Thr Ser Ser Gln Cys Ser Lys Pro Gly Val Ile Phe
    50                  55                  60

Leu Thr Lys Arg Ser Arg Gln Val Cys Ala Asp Pro Ser Glu Glu Trp
65                  70                  75                  80

Val Gln Lys Tyr Val Ser Asp Leu Glu Leu Ser Ala Gly Ser Gly Ser
                85                  90                  95

Gly Ser Gly Ser Gly Ser Glu Ser Lys Tyr Gly Pro Pro Cys Pro Ser
            100                 105                 110

Cys Pro Ala Pro Glu Phe Glu Gly Ala Pro Ser Val Phe Leu Phe Pro
        115                 120                 125

Pro Lys Pro Lys Asp Thr Leu Met Ile Ser Arg Thr Pro Glu Val Thr
    130                 135                 140

Cys Val Val Val Asp Val Ser Gln Glu Asp Pro Glu Val Gln Phe Asn
```

-continued

```
            145                 150                 155                 160
Trp Tyr Val Asp Gly Val Glu Val His Asn Ala Lys Thr Lys Pro Arg
                165                 170                 175
Glu Glu Gln Phe Asn Ser Thr Tyr Arg Val Val Ser Val Leu Thr Val
            180                 185                 190
Leu His Gln Asp Trp Leu Asn Gly Lys Glu Tyr Lys Cys Lys Val Ser
        195                 200                 205
Asn Lys Gly Leu Pro Ser Ser Ile Glu Lys Thr Ile Ser Lys Ala Lys
    210                 215                 220
Gly Gln Pro Arg Glu Pro Gln Val Tyr Thr Leu Pro Pro Ser Gln Glu
225                 230                 235                 240
Glu Met Thr Lys Asn Gln Val Ser Leu Thr Cys Leu Val Lys Gly Phe
                245                 250                 255
Tyr Pro Ser Asp Ile Ala Val Glu Trp Glu Ser Asn Gly Gln Pro Glu
            260                 265                 270
Asn Asn Tyr Lys Thr Thr Pro Pro Val Leu Asp Ser Asp Gly Ser Phe
        275                 280                 285
Phe Leu Tyr Ser Arg Leu Thr Val Asp Lys Ser Arg Trp Gln Glu Gly
    290                 295                 300
Asn Val Phe Ser Cys Ser Val Met His Glu Ala Leu His Asn His Tyr
305                 310                 315                 320
Thr Gln Lys Ser Leu Ser Leu Ser Leu Gly Lys
                325                 330
```

(2) INFORMATION FOR SEQ ID NO: 6:

(i) SEQUENCE CHARACTERISTICS:
        (A) LENGTH: 1234 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO: 6:

```
GCGGCCGCCC AATCATGCAG GTCTCCACTG CTGCCCTTGC TGTCCTCCTC TGCACCATGG      60
CTCTCTGCAA CCAGTTCTCT GCATCACTTG CTGCTGACAC GCCGACCGCC TGCTGCTTCA     120
GCTACACCTC CCGGCAGATT CCACAGAATT TCATAGCTGA CTACTTTGAG ACGAGCAGCC     180
AGTGCTCCAA GCCCGGTGTC ATCTTCCTAA CCAAGCGAAG CCGGCAGGTC TGTGCTGACC     240
CCAGTGAGGA GTGGGTCCAG AAATACGTCA GTGACCTGGA GCTGAGTGCC GGATCCGGCT     300
CTGGAGCGG CTCTGGCTCT GAGTCCAAAT ATGGTCCCCC ATGCCCATCA TGTCCAGGTA     360
AGCCAACCCA GGCCTCGCCC TCCAGCTCAA GGCGGGACAG GTGCCCTAGA GTAGCCTGCA     420
TCCAGGGACA GGCCCCAGCC GGGTGCTGAC GCATCCACCT CCATCTCTTC CTCAGCACCT     480
GAGTTCGAGG GGGCACCATC AGTCTTCCTG TTCCCCCCAA AACCCAAGGA CACTCTCATG     540
ATCTCCCGGA CCCCTGAGGT CACGTGCGTG GTGGTGGACG TGAGCCAGGA AGACCCCGAG     600
GTCCAGTTCA ACTGGTACGT GGATGGCGTG GAGGTGCATA ATGCCAAGAC AAAGCCGCGG     660
GAGGAGCAGT TCAACAGCAC GTACCGTGTG GTCAGCGTCC TCACCGTCCT GCACCAGGAC     720
TGGCTGAACG GCAAGGAGTA CAAGTGCAAG GTCTCCAACA AAGGCCTCCC GTCCTCCATC     780
GAGAAAACCA TCTCCAAAGC CAAAGGTGGG ACCCACGGGG TGCGAGGGCC ACACGGACAG     840
AGGTCAGCTC GGCCCACCCT CTGCCCTGGG AGTGACCGCT GTGCCAACCT CTGTCCCTAC     900
AGGGCAGCCC CGAGAGCCAC AGGTGTACAC CCTGCCCCCA TCCCAGGAGG AGATGACCAA     960
```

-continued

```
GAACCAGGTC AGCCTGACCT GCCTGGTCAA AGGCTTCTAC CCCAGCGACA TCGCCGTGGA    1020

GTGGGAGAGC AATGGGCAGC CGGAGAACAA CTACAAGACC ACGCCTCCCG TGCTGGACTC    1080

CGACGGCTCC TTCTTCCTCT ACAGCAGGCT AACCGTGGAC AAGAGCAGGT GGCAGGAGGG    1140

GAATGTCTTC TCATGCTCCG TGATGCATGA GGCTCTGCAC AACCACTACA CACAGAAGAG    1200

CCTCTCCCTG TCTCTGGGTA AATGATAAGA ATTC                                1234
```

(2) INFORMATION FOR SEQ ID NO: 7:

(i) SEQUENCE CHARACTERISTICS:
        (A) LENGTH: 331 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 7:

```
Met Lys Leu Cys Val Thr Val Leu Ser Leu Leu Met Leu Val Ala Ala
1               5                   10                  15

Phe Cys Ser Pro Ala Leu Ser Ala Pro Met Gly Ser Asp Pro Pro Thr
            20                  25                  30

Ala Cys Cys Phe Ser Tyr Thr Ala Arg Lys Leu Pro Arg Asn Phe Val
        35                  40                  45

Val Asp Tyr Tyr Glu Thr Ser Ser Leu Cys Ser Gln Pro Ala Val Val
    50                  55                  60

Phe Gln Thr Lys Arg Ser Lys Gln Val Cys Ala Asp Pro Ser Glu Ser
65                  70                  75                  80

Trp Val Gln Glu Tyr Val Tyr Asp Leu Glu Leu Asn Gly Ser Gly Ser
                85                  90                  95

Gly Ser Gly Ser Gly Ser Glu Ser Lys Tyr Gly Pro Pro Cys Pro Ser
            100                 105                 110

Cys Pro Ala Pro Glu Phe Glu Gly Ala Pro Ser Val Phe Leu Phe Pro
        115                 120                 125

Pro Lys Pro Lys Asp Thr Leu Met Ile Ser Arg Thr Pro Glu Val Thr
    130                 135                 140

Cys Val Val Val Asp Val Ser Gln Glu Asp Pro Glu Val Gln Phe Asn
145                 150                 155                 160

Trp Tyr Val Asp Gly Val Glu Val His Asn Ala Lys Thr Lys Pro Arg
                165                 170                 175

Glu Glu Gln Phe Asn Ser Thr Tyr Arg Val Val Ser Val Leu Thr Val
            180                 185                 190

Leu His Gln Asp Trp Leu Asn Gly Lys Glu Tyr Lys Cys Lys Val Ser
        195                 200                 205

Asn Lys Gly Leu Pro Ser Ser Ile Glu Lys Thr Ile Ser Lys Ala Lys
    210                 215                 220

Gly Gln Pro Arg Glu Pro Gln Val Tyr Thr Leu Pro Pro Ser Gln Glu
225                 230                 235                 240

Glu Met Thr Lys Asn Gln Val Ser Leu Thr Cys Leu Val Lys Gly Phe
                245                 250                 255

Tyr Pro Ser Asp Ile Ala Val Glu Trp Glu Ser Asn Gly Gln Pro Glu
            260                 265                 270

Asn Asn Tyr Lys Thr Thr Pro Pro Val Leu Asp Ser Asp Gly Ser Phe
        275                 280                 285

Phe Leu Tyr Ser Arg Leu Thr Val Asp Lys Ser Arg Trp Gln Glu Gly
```

```
                290                 295                 300
Asn Val Phe Ser Cys Ser Val Met His Glu Ala Leu His Asn His Tyr
305                 310                 315                 320

Thr Gln Lys Ser Leu Ser Leu Ser Leu Gly Lys
                325                 330

(2) INFORMATION FOR SEQ ID NO: 8:

(i) SEQUENCE CHARACTERISTICS:
        (A) LENGTH: 1235 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO: 8:

GCGGCCGCCA ATACCATGAA GCTCTGCGTG ACTGTCCTGT CTCTCCTCAT GCTAGTAGCT       60
GCCTTCTGCT CTCCAGCGCT CTCAGCACCA ATGGGCTCAG ACCCTCCCAC CGCCTGCTGC      120
TTTTCTTACA CCGCGAGGAA GCTTCCTCGC AACTTTGTGG TAGATTACTA TGAGACCAGC      180
AGCCTCTGCT CCCAGCCAGC TGTGGTATTC CAAACCAAAA GAAGCAAGCA AGTCTGTGCT      240
GATCCCAGTG AATCCTGGGT CCAGGAGTAC GTGTATGACC TGGAACTGAA CGGATCCGGC      300
TCTGGGAGCG GCTCTGGCTC TGAGTCCAAA TATGGTCCCC CATGCCCATC ATGTCCAGGT      360
AAGCCAACCC AGGCCTCGCC CTCCAGCTCA AGGCGGGACA GGTGCCCTAG AGTAGCCTGC      420
ATCCAGGGAC AGGCCCCAGC CGGGTGCTGA CGCATCCACC TCCATCTCTT CCTCAGCACC      480
TGAGTTCGAG GGGGCACCAT CAGTCTTCCT GTTCCCCCCA AAACCCAAGG ACACTCTCAT      540
GATCTCCCGG ACCCCTGAGG TCACGTGCGT GGTGGTGGAC GTGAGCCAGG AAGACCCCGA      600
GGTCCAGTTC AACTGGTACG TGGATGGCGT GGAGGTGCAT AATGCCAAGA CAAAGCCGCG      660
GGAGGAGCAG TTCAACAGCA CGTACCGTGT GGTCAGCGTC CTCACCGTCC TGCACCAGGA      720
CTGGCTGAAC GGCAAGGAGT ACAAGTGCAA GGTCTCCAAC AAAGGCCTCC CGTCCTCCAT      780
CGAGAAAACC ATCTCCAAAG CCAAAGGTGG GACCCACGGG GTGCGAGGGC CACACGGACA      840
GAGGTCAGCT CGGCCCACCC TCTGCCCTGG GAGTGACCGC TGTGCCAACC TCTGTCCCTA      900
CAGGGCAGCC CCGAGAGCCA CAGGTGTACA CCCTGCCCCC ATCCCAGGAG GAGATGACCA      960
AGAACCAGGT CAGCCTGACC TGCCTGGTCA AAGGCTTCTA CCCCAGCGAC ATCGCCGTGG     1020
AGTGGGAGAG CAATGGGCAG CCGGAGAACA ACTACAAGAC CACGCCTCCC GTGCTGGACT     1080
CCGACGGCTC CTTCTTCCTC TACAGCAGGC TAACCGTGGA CAAGAGCAGG TGGCAGGAGG     1140
GGAATGTCTT CTCATGCTCC GTGATGCATG AGGCTCTGCA CAACCACTAC ACACAGAAGA     1200
GCCTCTCCCT GTCTCTGGGT AAATGATAAG AATTC                                1235

(2) INFORMATION FOR SEQ ID NO: 9:

(i) SEQUENCE CHARACTERISTICS:
        (A) LENGTH: 92 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 9:

Met Gln Val Ser Thr Ala Ala Leu Ala Val Leu Leu Cys Thr Met Ala
1               5                   10                  15
```

-continued

```
Leu Cys Asn Gln Phe Ser Ala Ser Leu Ala Ala Asp Thr Pro Thr Ala
            20                  25                  30

Cys Cys Phe Ser Tyr Thr Ser Arg Gln Ile Pro Gln Asn Phe Ile Ala
        35                  40                  45

Asp Tyr Phe Glu Thr Ser Ser Gln Cys Ser Lys Pro Gly Val Ile Phe
    50                  55                  60

Leu Thr Lys Arg Ser Arg Gln Val Cys Ala Asp Pro Ser Glu Glu Trp
65              70                  75                  80

Val Gln Lys Tyr Val Ser Asp Leu Glu Leu Ser Ala
                85                  90

(2) INFORMATION FOR SEQ ID NO: 10:

(i) SEQUENCE CHARACTERISTICS:
        (A) LENGTH: 92 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 10:

Met Lys Leu Cys Val Thr Val Leu Ser Leu Leu Met Leu Val Ala Ala
1               5                   10                  15

Phe Cys Ser Pro Ala Leu Ser Ala Pro Met Gly Ser Asp Pro Pro Thr
            20                  25                  30

Ala Cys Cys Phe Ser Tyr Thr Ala Arg Lys Leu Pro Arg Asn Phe Val
        35                  40                  45

Val Asp Tyr Tyr Glu Thr Ser Ser Leu Cys Ser Gln Pro Ala Val Val
    50                  55                  60

Phe Gln Thr Lys Arg Ser Lys Gln Val Cys Ala Asp Pro Ser Glu Ser
65              70                  75                  80

Trp Val Gln Glu Tyr Val Tyr Asp Leu Glu Leu Asn
                85                  90
```

CHIMERIC POLYPEPTIDES CONTAINING CHEMOKINE DOMAINS

This application is a continuation of application Ser. No. 09/467,638, filed Dec. 20, 1999 now U.S. Pat. No. 6,730,296, which is a divisional of application Ser. No. 08/808,720, filed Feb. 28, 1997, now U.S. Pat. No. 6,100,387.

BACKGROUND OF THE INVENTION

The present invention relates generally to chimeric polypeptides containing chemokine polypeptide domains. More specifically, the invention relates to the expression in host cells of recombinant polynucleotide sequences encoding chemokine polypeptides covalently attached to heterologous polypeptides, and the use of such chimeric polypeptides as research tools for identifying chemokine receptors, as vaccine adjuvants, as agents-for the chemotactic recruitment of migratory cells, as agents for the stimulation or inhibition of angiogenesis, as agents against autoimmune diseases and inflammation, and as agents to inhibit the binding of HIV to certain receptors.

Chemokines (or chemotactic cytokines) are a class of cytokine molecules capable of chemotactically attracting migratory cells, and are involved in cell recruitment and activation in inflammation. Chemokines generally have small molecular weights in the range of 8-10 kDa and, like other small proteins such as cytokines, are believed to be rapidly inactivated in vivo, resulting in relatively short biological half-lives for these proteins. Most chemokines can be divided into two subgroups, CXC or CC, on the basis of the spacing of two highly-conserved cysteine amino acids near the amino terminus of these proteins. Within the CXC and CC subgroups, chemokines are further grouped into related families based on amino acid sequence similarity between them. CXC chemokine families include the IP-10 and Mig family; the GROα, GROβ, and GROγ family; the interleukin-8 (IL-8) family; and the PF4 family. CC chemokine families include the monocyte chemoattractant protein (MCP) family; the family including macrophage inhibitory protein-1α (MIP-1α), macrophage inhibitory protein-1β (MIP-1β), and regulated on activation normal T cell expressed (RANTES); and the lymphotactin family. The chemokines stromal cell-derived factor 1α (SDF-1α) and stromal cell-derived factor 1β (SDF-1β) form a chemokine family that is approximately equally related by amino acid sequence similarity to the CXC and CC chemokine subgroups. Individual members of the chemokine families are known to be bound by at least one chemokine receptor, with CXC chemokines generally bound by members of the CXCR class of receptors, and CC chemokines by members of the CCR class of receptors. For example, SDF-1α is known to be a ligand for the CXCR receptor fusin/CXCR4, and MIP-1α is bound by the CCR receptors CCR1, CCR4, and CCR5.

The presence of a chemokine gradient attracts migratory cells such as lymphocytes, leukocytes, and antigen-presenting cells (APCs) that may participate in autoimmune reactions, inflammation, or normal immune responses, or that may release other intercellular factors to stimulate or inhibit angiogenesis or other cellular processes. For example, the initiation of autoimmune disease requires the infiltration or recruitment of lymphocytes able to respond against self proteins into the organ bearing the antigenic self proteins. Inflammatory atherosclerotic lesions are due in part to infiltration of the vascular compartment by leukocytes recruited to the site. To induce an immune response, antigenic proteins and glycoproteins must bind to the surface of B lymphocytes to stimulate antibody production, and must be taken up by antigen-presenting cells, processed, and represented to T lymphocytes to mediate a T-lymphocyte response. Migratory cells that secrete IP10 or IL-8, when attracted by a chemokine gradient to a particular site, respectively may inhibit or stimulate the formation of blood vessels at that site. Chemokines may be used to establish a chemoattractive gradient for migratory cells that are expressing the appropriate chemokine receptors, or to obscure an existing chemoattractive gradient.

Chemokine receptors are also involved in functions other than chemotaxis, such as interacting with viral proteins. HIV-1 is known to bind to certain proteins on the surface of cells in order to gain entrance into these cells and replicate or integrate the viral gene into the host DNA. The CD4 protein on T lymphocytes and other cells, including certain antigen presenting cells, has been shown to be bound by the HIV-1 viral envelope protein gp120. This is believed to induce in gp120 a conformational change that then exposes regions of gp120 and perhaps CD4 that subsequently bind to a chemokine receptor. To date CXCR4 (also known as fusin), CCR5, and several other chemokine receptors have been identified as co-receptors for HIV-1. Monocyte-tropic (M-tropic) isolates of HIV-1 require interaction with CCR5 in order to infect cells, while T-lymphocyte-tropic (T-tropic) HIV-1 isolates require another coreceptor, CXCR4, for infection. There is some evidence indicating that HIV-1 can also use other CCR receptors such as CCR2 and CCR3 to gain entry into cells expressing them. For some HIV-2 isolates, it appears that certain chemokine receptors such as fusin/CXCR4 alone can provide the cell-surface protein needed for binding and entrance into the cell.

HIV-1 infection of cells expressing CD4 and fusin/CXCR4 is greatly decreased by the addition of purified SDF-1α, which is bound by fusin/CXCR4. We have found that preincubation of cells in the presence of purified SDF-1α for a short period of time at 37° C. causes a profound down-regulation of the receptor. This down-regulation of fusin/CXCR4 correlates with a decrease in the ability of HIV-1 to infect cells.

There is a continuing requirement for new compositions that will enhance, alter, or inhibit the effects of chemokine-receptor interactions, and for methods for their use.

SUMMARY OF THE INVENTION

Applicants have for the first time constructed novel chimeric DNA molecules encoding chimeric polypeptides comprising chemokine polypeptide domains. Chimeric polypeptides expressed from these constructs have exhibited novel properties, including novel interactions with cells expressing chemokine receptors.

In one embodiment, the present invention provides a composition comprising an isolated polynucleotide encoding a chimeric polypeptide, the chimeric polypeptide comprising at least one chemokine polypeptide covalently attached to at least one heterologous polypeptide. Preferably, the chemokine polypeptide is SDF-1α, MIP-1α, or MIP-1β, or is derived from SDF-1α, MIP-1α, or MIP-1β. Preferably, the heterologous polypeptide is an Fc polypeptide.

Another embodiment provides a composition comprising an isolated polynucleotide encoding a chimeric polypeptide, wherein a heterologous polypeptide is covalently attached to the amino terminus of a chemokine polypeptide, preferably by a linker polypeptide.

Another embodiment provides a composition comprising an isolated polynucleotide encoding a chimeric polypeptide, wherein a heterologous polypeptide is covalently attached to the carboxyl terminus of a chemokine polypeptide, preferably by a linker polypeptide.

In another embodiment, the present invention provides a composition comprising an isolated polynucleotide encoding a chimeric polypeptide, wherein the polynucleotide is selected from the group consisting of:

(a) a polynucleotide comprising the nucleotide sequence of SEQ ID NO:2 from nucleotide 12 to nucleotide 1213;

(b) a polynucleotide comprising the nucleotide sequence of SEQ ID NO:2 from nucleotide 69 to nucleotide 1213;

(c) a polynucleotide comprising the nucleotide sequence of SEQ ID NO:2 from nucleotide 72 to nucleotide 1213;

(d) a polynucleotide comprising the nucleotide sequence of SEQ ID NO:2 from nucleotide 75 to nucleotide 1213;

(e) a polynucleotide comprising a fragment of the nucleotide sequence of SEQ ID NO:2;

(f) a polynucleotide comprising the nucleotide sequence of the full-length protein-coding sequence of clone S1-3 deposited under accession number ATCC 98338;

(g) a polynucleotide comprising the nucleotide sequence of the mature protein-coding sequence of clone S1-3 deposited under accession number ATCC 98338;

(h) a polynucleotide encoding a chimeric polypeptide comprising the amino acid sequence of SEQ ID NO:1;

(i) a polynucleotide encoding a chimeric polypeptide comprising the amino acid sequence of SEQ ID NO:1 from amino acid 20 to amino acid 328;

(j) a polynucleotide encoding a chimeric polypeptide comprising the amino acid sequence of SEQ ID NO:1 from amino acid 22 to amino acid 328;

(k) a polynucleotide encoding a chimeric polypeptide comprising a fragment of the amino acid sequence of SEQ ID NO:1;

(l) a polynucleotide comprising a nucleotide sequence complementary to any one of the polynucleotides specified in (a)-(k) above; and (m) a polynucleotide capable of simultaneously hybridizing under stringent conditions to sequences encoding the chemokine polypeptide and to sequences encoding the heterologous polypeptide in any one of the polynucleotides specified in (a)-(l) above.

Preferably, such polynucleotide comprises the nucleotide sequence of SEQ ID NO:2 from nucleotide 12 to nucleotide 1213; the nucleotide sequence of the full-length protein-coding sequence of clone S1-3 deposited under accession number ATCC 98338; or the nucleotide sequence of the mature protein-coding sequence of clone S1-3 deposited under accession number ATCC 98338.

In a further embodiment, the present invention provides a composition comprising an isolated polynucleotide encoding a chimeric polypeptide, wherein the polynucleotide is selected from the group consisting of:

(a) a polynucleotide comprising the nucleotide sequence of SEQ ID NO:4 from nucleotide 12 to nucleotide 1207;

(b) a polynucleotide comprising the nucleotide sequence of SEQ ID NO:4 from nucleotide 69 to nucleotide 1207;

(c) a polynucleotide comprising a fragment of the nucleotide sequence of SEQ ID NO:4;

(d) a polynucleotide comprising the nucleotide sequence of the full-length protein-coding sequence of clone SK2-2 deposited under accession number ATCC 98339;

(e) a polynucleotide comprising the nucleotide sequence of the mature protein-coding sequence of clone SK-2 deposited under accession number ATCC 98339;

(f) a polynucleotide encoding a chimeric polypeptide comprising the amino acid sequence of SEQ ID NO:3;

(g) a polynucleotide encoding a chimeric polypeptide comprising the amino acid sequence of SEQ ID NO:3 from amino acid 20 to amino acid 326;

(h) a polynucleotide encoding a chimeric polypeptide comprising a fragment of the amino acid sequence of SEQ ID NO:3;

(i) a polynucleotide comprising a nucleotide sequence complementary to any one of the polynucleotides specified in (a)-(h) above; and (j) a polynucleotide capable of simultaneously hybridizing under stringent conditions to sequences encoding the chemokine polypeptide and to sequences encoding the heterologous polypeptide in any one of the polynucleotides specified in (a)-(i) above.

Preferably, such polynucleotide comprises the nucleotide sequence of SEQ ID NO:4 from nucleotide 12 to nucleotide 1207; the nucleotide sequence of the full-length protein-coding sequence of clone SK2-2 deposited under accession number ATCC 98339; or the nucleotide sequence of the mature protein-coding sequence of clone SK2-2 deposited under accession number ATCC 98339.

In another embodiment, the present invention provides a composition comprising an isolated polynucleotide encoding a chimeric polypeptide, wherein the polynucleotide is selected from the group consisting of:

(a) a polynucleotide comprising the nucleotide sequence of SEQ ID NO:6 from nucleotide 15 to nucleotide 1225;

(b) a polynucleotide comprising the nucleotide sequence of SEQ ID NO:6 from nucleotide 81 to nucleotide 1225;

(c) a polynucleotide comprising a fragment of the nucleotide sequence of SEQ ID NO:6;

(d) a polynucleotide comprising the nucleotide sequence of the full-length protein-coding sequence of clone MP-1 deposited under accession number ATCC 98431;

(e) a polynucleotide comprising the nucleotide sequence of the full-length protein-coding sequence of clone MP-2 deposited under accession number ATCC 98431;

(f) a polynucleotide comprising the nucleotide sequence of the full-length protein-coding sequence of clone MP-6 deposited under accession number ATCC XXXXX;

(g) a polynucleotide comprising the nucleotide sequence of the mature protein-coding sequence of clone MP-1 deposited under accession number ATCC XXXXX;

(e) a polynucleotide comprising the nucleotide sequence of the full-length protein-coding sequence of clone MP-2 deposited under accession number ATCC 98342;

(f) a polynucleotide comprising the nucleotide sequence of the full-length protein-coding sequence of MP-6 deposited under accession number ATCC 98340;

(g) a polynucleotide comprising the nucleotide sequence of the full-length protein-coding sequence of MP-1 deposited under accession number ATCC 98341;

(h) a polynucleotide comprising the nucleotide sequence of the mature protein-coding sequence of clone MP-2 deposited under accession number ATCC 98342;

(i) a polynucleotide comprising the nucleotide sequence of the full-length protein-coding sequence of MP-6 deposited under accession number ATCC 98340;

(j) a polynucleotide encoding a chimeric polypeptide comprising the amino acid sequence of SEQ ID NO:5;

(k) a polynucleotide encoding a chimeric polypeptide comprising the amino acid sequence of SEQ ID NO:5 from amino acid 23 to amino acid 331;

(l) a polynucleotide encoding a chimeric polypeptide comprising a fragment of the amino acid sequence of SEQ ID NO:5;

(m) a polynucleotide comprising a nucleotide sequence complementary to any one of the polynucleotides specified in (a)-(l) above; and (n) a polynucleotide capable of simultaneously hybridizing under stringent conditions to sequences encoding the chemokine polypeptide and to sequences encoding the heterologous polypeptide in any one of the polynucleotides specified in (a)-(m) above.

Preferably, such polynucleotide comprises the nucleotide sequence of SEQ ID NO:6 from nucleotide 15 to nucleotide 1225; the nucleotide sequence of the full-length protein-coding sequence of clones MP-1, MP-2, and MP-6 deposited under accession numbers ATCC 98431, ATCC 98432, and ATCC 98430, respectively; or the nucleotide sequence of the mature protein-coding of clones MP-1, MP-2, and MP-6 deposited under accession numbers ATCC 98431, ATCC 98432, and ATCC 98430, respectively.

In a further embodiment, the present invention provides a composition comprising an isolated polynucleotide encoding a chimeric polypeptide, wherein the polynucleotide is selected from the group consisting of:

(a) a polynucleotide comprising the nucleotide sequence of SEQ ID NO:8 from nucleotide 16 to nucleotide 1226;

(b) a polynucleotide comprising the nucleotide sequence of SEQ ID NO:8 from nucleotide 85 to nucleotide 1226;

(c) a polynucleotide comprising a fragment of the nucleotide sequence of SEQ ID NO:8;

(d) a polynucleotide encoding a chimeric polypeptide comprising the amino acid sequence of SEQ ID NO:7;

(e) a polynucleotide encoding a chimeric polypeptide comprising the amino acid sequence of SEQ ID NO:7 from amino acid 24 to amino acid 331;

(f) a polynucleotide encoding a chimeric polypeptide comprising a fragment of the amino acid sequence of SEQ ID NO:7;

(g) a polynucleotide comprising a nucleotide sequence complementary to any one of the polynucleotides specified in (a)-(h) above; and (h) a polynucleotide capable of simultaneously hybridizing under stringent conditions to sequences encoding the chemokine polypeptide and to sequences encoding the heterologous polypeptide in any one of the polynucleotides specified in (a)-(i) above.

In certain preferred embodiments, the polynucleotide is operably linked to an is expression control sequence. The invention also provides a host cell, preferably a mammalian cell, transformed with such polynucleotide compositions.

Processes are also provided for producing a chimeric polypeptide, which comprise:

(a) growing a culture of the host cell transformed with such polynucleolide compositions in a suitable culture medium; and (b) purifying the protein from the culture.

The polypeptide produced according to such methods is also provided by the present invention. Preferred embodiments include those in which the polypeptide produced by such process is a mature form of the polypeptide.

In other embodiments, the present invention provides a composition comprising 5 a chimeric polypeptide, the chimeric polypeptide comprising at least one chemokine polypeptide covalently attached to at least one heterologous polypeptide. Preferably, the chemokine polypeptide is SDF-1α, MIP-1α, or MIP-1β, or is derived from SDF-1α, MIP-1α, or MIP-1β. Preferably, the heterologous polypeptide is an Fc polypeptide.

A further embodiment provides a composition comprising a chimeric polypeptide, wherein a heterologous polypeptide is covalently attached to the amino terminus of a chemokine polypeptide, preferably by a linker polypeptide.

Another embodiment provides a composition comprising a chimeric polypeptide, wherein a heterologous polypeptide is covalently attached to the carboxyl terminus of a chemokine polypeptide, preferably by a linker polypeptide.

In another embodiment, the present invention provides a composition comprising a chimeric polypeptide, wherein the chimeric polypeptide comprises an amino acid sequence selected from the group consisting of:

(a) the amino acid sequence of SEQ ID NO:1;

(b) the amino acid sequence of SEQ ID NO:1 from amino acid 20 to amino acid 328;

(c) the amino acid sequence of SEQ ID NO:1 from amino acid 21 to amino acid 328;

(d) the amino acid sequence of SEQ ID NO:1 from amino acid 22 to amino acid 328; and (e) fragments of the amino acid sequence of SEQ ID NO:1.

Preferably, such chimeric polypeptide comprises the amino acid sequence of SEQ ID NO:1.

In a further embodiment, the present invention provides a composition comprising a chimeric polypeptide, wherein the chimeric polypeptide comprises an amino acid sequence selected from the group consisting of:

(a) the amino acid sequence of SEQ ID NO:3;

(b) the amino acid sequence of SEQ ID NO:3 from amino acid 20 to amino acid 326; and (c) fragments of the amino acid sequence of SEQ ID NO:3.

Preferably, such chimeric polypeptide comprises the amino acid sequence of SEQ ID NO:3.

In another embodiment, the present invention provides a composition comprising a chimeric polypeptide, wherein the chimeric polypeptide comprises an amino acid sequence selected from the group consisting of:

(a) the amino acid sequence of SEQ ID NO:5;

(b) the amino acid sequence of SEQ ID NO:5 from amino acid 23 to amino acid 331; and (c) fragments of the amino acid sequence of SEQ ID NO:5.

Preferably, such chimeric polypeptide comprises the amino acid sequence of SEQ ID NO:5.

In a further embodiment, the present invention provides a composition comprising a chimeric polypeptide, wherein the chimeric polypeptide comprises an amino acid sequence selected from the group consisting of:

(a) the amino acid sequence of SEQ ID NO:7;

(b) the amino acid sequence of SEQ ID NO:7 from amino acid 24 to amino acid 331; and (c) fragments of the amino acid sequence of SEQ ID NO:7.

Preferably, such chimeric polypeptide comprises the amino acid sequence of SEQ ID NO:7.

Polypeptide compositions of the present invention may further comprise a pharmaceutically acceptable carrier. Compositions comprising an antibody which specifically reacts with such polypeptide are also provided by the present invention.

Methods are also provided for preventing, treating or ameliorating a medical condition which comprises administering a therapeutically effective amount of a composition comprising a polypeptide of the present invention and a pharmaceutically acceptable carrier.

The present invention also provides methods for identifying molecules capable of interacting with a chimeric polypeptide which comprise:

(a) combining a composition comprising a chimeric polypeptide with a composition comprising molecules to be tested for interaction, forming a first mixture;

(b) combining the first mixture with a composition comprising indicator molecules, so that the indicator molecules are capable of being altered by the first mixture; and (c) detecting the presence of altered indicator molecules.

Methods are also provided for attracting migratory cells to a region of an organism which comprises administering therapeutically effective amounts of at least one composition comprising a chimeric polypeptide.

Methods for stimulating or inhibiting angiogenesis, which comprise administering therapeutically effective amounts of at least one composition comprising a chimeric polypeptide, are also provided.

Methods are also provided for preventing, treating, or ameliorating an inflammatory or an autoimmune condition, which comprise administering therapeutically effective amounts of at least one composition comprising a chimeric polypeptide.

Methods for enhancing antigen-presenting cell activity, which comprise administering therapeutically effective amounts of at least one composition comprising a chimeric polypeptide, wherein at least one chimeric polypeptide comprises antigen molecules, are also provided.

Methods are provided for inducing an immune response which comprise administering a vaccine and therapeutically effective amounts of at least one composition comprising a chimeric polypeptide.

Methods for altering receptor function which comprise causing a receptor to bind at least one chimeric polypeptide, and for decreasing receptor function which comprise causing a receptor to bind at least one chimeric polypeptide, resulting in a decrease in the number of functional receptor molecules, are provided.

Methods are provided for preventing, treating, or ameliorating HIV infection which comprise administering therapeutically effective amounts of at least one composition comprising a chimeric polypeptide. Preferably, the chemokine polypeptide of the chimeric polypeptide comprises SDF-1α, MIP-1α, or MIP-1β.

Other aspects and advantages of the present invention will be apparent upon consideration of the following detailed description of preferred embodiments thereof.

BRIEF DESCRIPTION OF THE FIGURES

FIG. 1 shows the expression of chimeric polypeptides, described in Example 2.

FIG. 2 shows chimeric SDF-1α polypeptide binding to cells expressing the fusin/CXCR4 receptor, as described in Example 3.

DETAILED DESCRIPTION OF THE INVENTION

The present inventors have for the first time constructed novel chimeric polypeptides comprising a chemokine polypeptide covalently attached to a heterologous polypeptide. These chimeric polypeptides interact with chemokine receptors and have novel properties.

As used herein, "chemokine" includes all molecules with chemotactic activity or derived from molecules with chemotactic activity by any kind of alteration, addition, insertion, deletion, mutation, substitution, replacement, or modification. Chemotactic activity for a particular cell population is the direct or indirect stimulation of the directed orientation or movement of such cell population. Preferably, the cell population comprises circulating blood cells, bone marrow stem cells. More preferably, the cell population may include monocytes, B cells, T cells, basophils, eosinophils, neutrophils, natural killer (NK) cells, and bone marrow stem cells. Most preferably, the cell population may include monocytes, T cells, basophils, and bone marrow stem cells. Preferably, the chemokine has the ability to directly stimulate directed movement of cells. Whether a particular polypeptide has chemotactic activity for a population of cells can be readily determined by employing the polypeptide in any known assay for cell chemotaxis. Assays for chemotactic activity (which will identify proteins that induce or prevent chemotaxis) consist of assays that measure the ability of a protein to induce the migration of cells across a membrane as well as the ability of a protein to induce the adhesion of one cell population to another cell population. Suitable assays for movement and adhesion include, without limitation, those described in: Current Protocols in Immunology, Ed. by J. E. Coligan, A. M. Kruisbeek, D. H. Margulies, E. M. Shevach, W. Strober, Pub. by Greene Publishing Associates and Wiley-Interscience (Chapter 6.12, Measurement of alpha and beta Chemokines 6.12.1-6.12.28); Taub et al., J. Clin. Invest. 95:1370-1376, 1995; Lind et al., APMIS 103:140-146, 1995; Muller et al., Eur. J. Immunol. 25: 1744-1748; Gruber et al., J. of Immunol. 152:5860-5867, 1994; Johnston et al., J. of Immunol. 153: 1762-1768, 1994; all of which are incorporated herein by reference.

As used herein, "covalently attached" means the attachment of molecules to each other by covalent chemical bonds, either directly or through a linker molecule that is itself covalently attached to said molecules.

As used herein, "heterologous polypeptides" include all polypeptides that can be covalently attached to a chemokine polypeptide, including without limitation chemokines, cytokines, immunoglobulins, antigens, antibody-binding tags such as His, Flag, or myc, lectin-binding domains, toxins, kinases, proteases, other enzymes, structural proteins; polypeptides derived from the foregoing by any form of alteration, addition, insertion, deletion, mutation, substitution, replacement, or modification; but excluding thioredoxin. For example, chemokine polypeptides can be attached through "linker" sequences to the Fc portion of an immunoglobulin. For a bivalent form of the chemokine, such a fusion could be to the Fc portion of an IgG molecule. Other immunoglobulin isotypes may also be used to generate such fusions. For example, a chemokine-IgM fusion would generate a decavalent form of the chemokine. In addition, it is possible to create a multivalent form of a chimeric polypeptide by connecting the chimeric polypeptide through a Pi linkage to the phosphatidyl inositol present in micellular preparations.

Fragments of chimeric chemokine polypeptides are also encompassed by the present invention. Preferably, such fragments retain the desired activity of the polypeptide or modify it to create a desired activity. Fragments of polypeptides may be in linear form or they may be cyclized using known methods, for example, as described in H. U. Saragovi, et al., Bio/Technology 10, 773-778 (1992) and in R. S. McDowell, et al., J. Amer. Chem. Soc. 114, 9245-9253 (1992), both of which are incorporated herein by reference. The polypeptides provided herein also include polypeptides characterized by amino acid sequences similar to those of purified proteins but into which modification are naturally provided or deliberately engineered. For example, modifications in the polypeptide or DNA sequences can be made by those skilled in the art using known techniques. Modifications of interest in the polypeptide sequences may include the alteration, addition, insertion, deletion, mutation, substitution, replacement, or modification of a selected amino acid residue in the coding sequence. As one example, one or more of the cysteine residues may be deleted or replaced with another amino acid to alter the conformation of the molecule. As another example, an additional amino acid may be added to the N-terminus of the polypeptide. Also, the amino acid sequence of the polypeptide may be altered using random mutation techniques. It is also possible to attach to polypeptides other moieties, including without limitation carbohydrates, lipids, or polyethylene glycol, or to remove or alter such moieties. Techniques for such alterations, additions, insertions, deletions, mutations, substitutions, replacements, or modifications are well known to those skilled in the art (see, e.g., U.S. Pat. No. 4,518,584). Preferably, such alteration, addition, insertion, deletion, mutation, substitution, replacement, or modification retains the desired activity of the polypeptide or modifies it to create a desired activity.

Other fragments and derivatives of the sequences of polypeptides which would be expected to retain polypeptide activity and may thus be useful for screening or other immunological methodologies may also be easily made by those skilled in the art given the disclosures herein. Such modifications are believed to be encompassed by the present invention.

The present invention also provides both full-length and mature forms of chimeric chemokine polypeptides. The full-length form of such polypeptides is identified in the sequence listing by translation of the protein-coding region, excluding introns, of the nucleotide sequence of each disclosed construct. The mature form of such polypeptides may be obtained by expression of the disclosed full-length polynucleotide (preferably those deposited with ATCC) in a suitable mammalian cell, preferably CHO or COS cell, or other host cell. The sequence of the mature form of the polypeptide may also be determinable from the amino acid sequence of the full-length form.

Chimeric chemokine polypeptides including chemokine polypeptides that are species homologs of disclosed polypeptides are also provided by the present invention. Species homologs may be isolated and identified by making suitable probes or primers from the sequences provided herein and screening a suitable nucleic acid source from the desired species. The invention also encompasses allelic variants of the disclosed chemokine polypeptides or chemokine-encoding polynucleotides; that is, naturally-occurring alternative forms of the isolated polynucleotide which also encode polypeptides which are identical, homologous or related to that encoded by the polynucleotides.

The present invention also includes polynucleotides capable of hybridizing under stringent conditions, preferably highly stringent conditions, to polynucleotides described herein. Highly stringent conditions include, for example, 0.2×SSC at 65° C.; stringent conditions include, for example, 4×SSC at 65° C. or 50% formamide and 4×SSC at 42° C. Preferably, such hybridizing polynucleotides are at least 70% homologous by sequence identity (more preferably, at least 80% homologous; most preferably 90% or 95% homologous) with the polynucleotide of the present invention to which they hybridize.

Preferred Chimeric Polypeptides and Polynucleotides Encoding Them

Amino acid sequences of chimeric chemokine polypeptides are set forth below, along with the sequences of polynucleotides encoding them. In these chimeric polypeptides, the chemokine has been linked to an Fc polypeptide by a [Gly-Ser]$_5$ linker peptide. The polynucleotides encoding these chimeric polypeptides were derived from chemokine cDNA sequences and genomic Fc sequences, as described in Example 1 below.

The sequence of a polynucleotide encoding one such chimeric polypeptide including an SDF-1α domain is set forth in SEQ ID NO:2, with the protein-coding sequence (including introns) extending from nucleotide 12 to 1213. This polynucleotide has been identified as S1-2 or S1-3, the DNA sequences of these two constructs appearing to be identical. The amino acid sequence of the chimeric polypeptide encoded by S1-2 and S1-3 is set forth in SEQ ID NO:1. The chimeric polypeptide encoded by S1-2 and S1-3 is 328 amino acids in length, with the mature polypeptide produced by cleavage of the secretory leader sequence beginning at amino acid 20, 21 or 22 of SEQ ID NO:1, depending on how the polypeptide is processed. The polynucleotide construct S1-3 was deposited with the American Type Culture Collection on Feb. 28, 1997 and given the accession number 98338.

The sequence of a polynucleotide encoding another such chimeric polypeptide that includes a domain derived from SDF-1α domain is set forth in SEQ ID NO:4, with the protein-coding sequence (including introns) extending from nucleotide 12 to 1207. This polynucleotide has been identified as SK2-2. The amino acid sequence of the chimeric polypeptide encoded by SK2-2 is set forth in SEQ ID NO:3. The chimeric polypeptide encoded by SK2-2 is 326 amino acids in length, with the mature polypeptide produced by cleavage of the secretory leader sequence beginning at amino acid 20 of SEQ ID NO:3. The polypeptide encoded by SK2-2 differs from that encoded by S1-2 and S1-3 in that two amino acids have been deleted from the SK2-2 sequence so that cleavage of the secretory leader sequence is predicted to always produce a product beginning at amino acid 20 of SEQ ID NO:3. The polynucleotide construct SK2-2 was deposited with the American Type Culture Collection on Feb. 28, 1997 and given the accession number 98339.

The sequence of a polynucleotide encoding a chimeric polypeptide that includes an MIP-1α domain is set forth in SEQ ID NO:6, with the protein-coding sequence (including introns) extending from nucleotide 15 to 1225. This polynucleotide is identified as MP-1. The DNA sequence of MP-1 has been determined, and while the DNA sequences of MP-2 and MP-6 are anticipated to be identical to that of MP-1, these clones may contain come PCR-generated DNA sequence alterations. The amino acid sequence of the chimeric polypeptide encoded by MP-1, and presumably encoded by MP-2 and MP-6, is set forth in SEQ ID NO:5. The chimeric polypeptide encoded by MP-1 is 331 amino acids in length, with the mature polypeptide produced by cleavage of the secretory leader sequence beginning at amino acid 23 of SEQ ID NO:5. The polynucleotide constructs MP-1, MP-2, and MP-6 were deposited with the American Type Culture Collection on Feb. 28, 1997 and given the accession numbers ATCC 98431, ATCC 98432, and ATCC 98430 respectively.

The sequence of a polynucleotide encoding a chimeric polypeptide that includes an MIP-1β domain is set forth in SEQ ID NO:8, with the protein-coding sequence (including introns) extending from nucleotide 16 to 1226. This polynucleotide is identified as MPB-X. The amino acid sequence of the chimeric polypeptide encoded by MPB-X is set forth in SEQ ID NO:7. The chimeric polypeptide encoded by MPB-X is predicted to be 331 amino acids in length, with the mature polypeptide produced by cleavage of the secretory leader sequence beginning at amino acid 24 of SEQ ID NO:7.

Expression and Purification of Chimeric Polypeptides

The isolated polynucleotide of the invention may be operably linked to an expression control sequence such as the pMT2 or pED expression vectors disclosed in Kaufman et al., Nucleic Acids Res. 19, 4485-4490 (1991), in order to produce the protein recombinantly. Many suitable expression control sequences are known in the art. General methods of expressing recombinant proteins are also known and are exemplified in R. Kaufman, Methods in Enzymology 185, 537-566 (1990). As defined herein "operably linked" means that the isolated polynucleotide of the invention and an expression control sequence are situated within a vector or cell in such a way that the protein is expressed by a host cell which has been transformed (transfected) with the ligated polynucleotide/expression control sequence.

A number of types of cells may act as suitable host cells for expression of the protein. Mammalian host cells include, for example, monkey COS cells, Chinese Hamster Ovary (CHO) cells, human kidney 293 cells, human epidermal A431 cells, human Colo205 cells, 3T3 cells, CV-1 cells, other transformed primate cell lines, normal diploid cells, cell strains derived from in vitro culture of primary tissue, primary explants, HeLa cells, mouse L cells, BHK, HL-60, U937, HaK or Jurkat cells.

Alternatively, it may be possible to produce the protein in lower eukaryotes such as yeast or in prokaryotes such as bacteria. Potentially suitable yeast strains include *Saccharomyces cerevisiae, Schizosaccharomyces pombe, Kluyveromyces* strains, *Candida*, or any yeast strain capable of expressing heterologous proteins. Potentially suitable bacterial strains include *Escherichia coli, Bacillus subtilis, Salmonella typhimurium*, or any bacterial strain capable of expressing heterologous proteins. If the protein is made in yeast or bacteria, it may be necessary to modify the protein produced therein, for example by phosphorylation or glycosylation of the appropriate sites, in order to obtain the functional protein. Such covalent attachments may be accomplished using known chemical or enzymatic methods.

The protein may also be produced by operably linking the isolated polynucleotide of the invention to suitable control sequences in one or more insect expression vectors, and employing an insect expression system. Materials and methods for baculovirus/insect cell expression systems are commercially available in kit form from, e.g., Invitrogen, San Diego, Calif., U.S.A. (the MaxBac® kit), and such methods are well known in the art, as described in Summers and Smith, *Texas Agricultural Experiment Station Bulletin No* 1555 (1987), incorporated herein by reference. As used-herein, an insect cell capable of expressing a polynucleotide of the present invention is "transformed."

The protein of the invention may also be expressed as a product of transgenic animals, e.g., as a component of the milk of transgenic cows, goats, pigs, or sheep which are characterized by somatic or germ cells containing a nucleotide sequence encoding the protein.

Alternatively, the protein of the invention may also be expressed in a form which will facilitate purification. For example, it may be expressed as a fusion protein. such as those of maltose binding protein (MBP), glutathione-S-transferase (GST) or thioredoxin (TRX). Kits for expression and purification of such fusion proteins are commercially available from New England BioLabs (Beverly, Mass.), Pharmacia (Piscataway, N.J.) and InVitrogen, respectively. The protein can also be tagged with an epitope and subsequently purified by using a specific antibody directed to such epitope. One such epitope ("Flag") is commercially available from Kodak (New Haven, Conn.).

The protein of the invention may be prepared by culturing transformed host cells under culture conditions suitable to express the recombinant protein. The resulting expressed protein may then be purified from such culture (i.e., from culture medium or cell extracts) using known purification processes, such as gel filtration and ion exchange chromatography. The purification of the protein may also include an affinity column containing agents which will bind to the protein; one or more column steps over such affinity resins as concanavalin A-agarose, heparin-toyopearl® or Cibacrom blue 3GA Sepharose®; one or more steps involving hydrophobic interaction chromatography using such resins as phenyl ether, butyl ether, or propyl ether; or immunoaffinity chromatography.

Finally, one or more reverse-phase high performance liquid chromatography (RP-HPLC) steps employing hydrophobic RP-HPLC media, e.g., silica gel having pendant methyl or other aliphatic groups, can be employed to further purify the protein. Some or all of the foregoing purification steps, in various combinations, can also be employed to provide a substantially homogeneous isolated recombinant protein. The protein thus purified is substantially free of other mammalian proteins and is defined in accordance with the present invention as an "isolated protein."

The protein may also be produced by known conventional chemical synthesis. Methods for constructing the proteins of the present invention by synthetic means are known to those skilled in the art. The synthetically-constructed protein sequences, by virtue of sharing primary, secondary or tertiary structural and/or conformational characteristics with proteins may possess biological properties in common therewith, including protein activity. Thus, they may be employed as biologically active or immunological substitutes for natural, purified proteins in screening of therapeutic compounds and in immunological processes for the development of antibodies.

Uses of Chimeric Polypeptides

Chimeric chemokine polypeptides can be used as tools for identifying cells expressing receptor for the chemokine, or for studying binding of chemokine to isolated receptor molecules. The construct when incubated with cells expressing a receptor for the chemokine will bind to these cells and can be indicated using a commercially available fluorescently tagged antibody, or other protein, able to bind to the heterologous polypeptide domain, such as the Fc region of human immunoglobulin, of the chimeric polypeptide. This will indicate cells having a surface receptor for a given chemokine as well as the density of this receptor on the cell surface.

Interactions between chimeric chemokine polypeptides and chemokine receptors can also be detected directly by measuring changes in surface plasmon resonance using a Biacore sensor (Pharmacia). The chemokine receptor or the chimeric polypeptide can be covalently immobilized to different flow cells on the Biacore sensor chip as recommended by the manufacturer. Molecules to be tested for interaction are then injected across the flow cells and binding is detected as a change in resonance units, a reflection of the mass of protein bound to the sensor chip surface.

Other suitable assays for receptor-ligand activity include without limitation those described in: Current Protocols in Immunology, edited by J. E. Coligan, A. M. Kruisbeek, D. H. Margulies, E. M. Shevach, W. Strober, published by Greene Publishing Associates and Wiley-Interscience (Chapter 7.28, Measurement of Cellular Adhesion under static conditions 7.28.1-7.28.22); Takai et al., Proc. Natl. Acad. Sci. USA 84:6864-6868, 1987; Bierer et al., J. Exp. Med. 168:1145-

1156, 1988; Rosenstein et al., J. Exp. Med. 169:149-160 1989; Stoltenborg et al., J. Immunol. Methods 175:59-68, 1994; Stitt et al., Cell 80:661-670, 1995; all of which are incorporated herein by reference.

Chimeric chemokine polypeptides can also be used as vaccine adjuvants. Proteins and glycoproteins injected to induce an immune response must bind to surface of B lymphocytes to stimulate antibody production and must be taken up by antigen presenting cells, processed, and represented to T lymphocytes to mediate a T lymphocyte response. By including with the antigen injection a chimeric chemokine-Fc polypeptide the infiltration of the necessary APCs and lymphocytes will be induced by the chemoattractive presence of the chemokine. One advantage of including an Fc domain in the chimeric polypeptide is that the chimeric polypeptide will have a longer biological half life than the chemokine alone would have. Also, by including in the chimeric polypeptide an Fc domain able to bind to existing Fc-receptors on cells at the site of injection, the chemokine activity will be concentrated at the site, much like a depot so that the chemokine gradient could be maintained over a long enough period of time to ensure the infiltration of the necessary responding cell populations.

Chimeric chemokine polypeptides can also be used to enhance the activity of antigen-presenting cells (APCs). The presence of the chemokine domain of the chimeric polypeptide would chemotactically attract APCs. Additionally, an antigenic molecule could be included in the chimeric polypeptide for delivery to the APC. When such an antigen-containing chimeric polypeptide binds to the surface of an APC and is internalized, and the chimeric polypeptide is degraded within the APC, the antigenic portion of the chimeric polypeptide would be freed for interaction with MHC proteins and presentation on the surface of the APC.

Chimeric chemokine polypeptides can also be used to affect the chemotactic recruitment of migratory cells. Chimeric chemokines may be used to establish a chemoattractive gradient for migratory cells that are expressing the appropriate chemokine receptors, or to obscure an existing chemoattractive gradient. By including a large or particularly stable heterologous polypeptide in the chimeric polypeptide, the chimeric polypeptide will have a longer biological half life and will be able to establish a longer lasting chemoattractive gradient, and will be more effective in obscuring a preexisting gradient. Also, a heterologous polypeptide domain may be selected that, by binding to particular molecules or cells, will target the chimeric chemokine polypeptide to a particular site in order to establish a chemoattractive gradient at that site. By altering chemoattractive gradients, chimeric chemokine polypeptides can be used to treat inflammatory and autoimmune disorders that require the recruitment of migratory cells. Also, by attracting to a particular site migratory cells that produce other intercellular factors such as IL-8 or IP-10, chimeric chemokine polypeptides may for example be used to stimulate angiogenesis at that site (if, for example, the recruited migratory cells were secreting IL-8) or to inhibit angiogenesis at that site (if, for example, the recruited migratory cells were secreting IP-10). In addition, by establishing a gradient of chimeric chemokine polypeptide within the bone marrow of a bone marrow transplant recipient, the chimeric chemokine polypeptide could be used to recruit the transplanted bone marrow cells to the bone marrow where they are needed. Similarly, other cellular processes could be affected by chimeric chemokine polypeptides, by using them to attract particular classes of migratory cells secreting determined factors.

Chimeric chemokine polypeptides can also be used to affect the nature of chemokine-receptor interactions, and may block the binding of endogenous molecules to their receptors. By binding to a receptor, chimeric chemokines may deliver a signal similar to that received via the normal ligand. When the heterologous polypeptide is an Fc polypeptide, because of its bivalent nature this signal may be delivered at a lower molar concentration of ligand. The signal delivered by binding the chimeric polypeptide may have some properties different from that of the normal ligand because of the structure of the chimeric polypeptide. This could include prolonged triggering/activation or decreased activation. The chimeric polypeptides, because of their larger size or the nature of the structure of the heterologous polypeptide domain, will have a longer half life in vivo compared to monomer ligand, possibly leading to prolonged signaling/activation. Also the larger size of the chimeric polypeptide will cause some satiric hindrance which may block the binding of the natural ligand. A chimeric chemokine polypeptide may desensitize a receptor's response to normal ligand by binding and inactivating further signaling through the same receptor. In the case where a receptor has more than one signaling function, the chimeric chemokine polypeptide may inhibit one form of signaling while enhancing or altering another. Also, a chimeric chemokine polypeptide may bind to a receptor and cause down regulation and/or internalization of the receptor. Additionally, a chimeric chemokine polypeptide may bind to a receptor and cause the internalization and destruction of the receptor, thus preventing it from recycling to the membrane surface. Also, by binding to one receptor a chimeric polypeptide may cause another receptor or membrane protein to become desensitized or unable to carry out its normal function.

Chimeric chemokine polypeptides can also be used to prevent infection of cells by HIV or other viruses by blocking the binding of virus to chemokine receptors. The chimeric chemokine polypeptide including SDF-1α and Fc polypeptides has been shown to bind to cells expressing the fusin/CXCR4 receptor. This binding will block HIV-1 isolates that are T-tropic from infecting fusin-positive cells in multiple ways: competing with HIV for existing chemokine receptors, down-regulation of the chemokine receptors by internalization, as well as desensitization of receptors required by HIV for infection. In a similar manner the construct consisting of an MIP-1α or MIP-1β polypeptide and an Fc polypeptide will bind to cells expressing the CCR5 receptor. This binding will block HIV-1 isolates that are M-tropic from infecting CCR5-positive cells in multiple ways: competing with HIV for existing chemokine receptors, down-regulation of the chemokine receptors by internalization, as well as desensitization of receptors required by HIV for infection. Alterations of the chimeric polypeptide, such as additions of amino acids at the N-terminus of the chemokine domain, may result in enhanced binding with loss of signaling, resulting in strong antagonism. By making chimeric chemokine polypeptides with several different chemokines a wide range of chemokine receptors can be inhibited or desensitized, thus blocking viral isolates that have mutated to infect cells using other chemokine receptors. It is also possible to modify a chemokine sequence so that it will bind to a wider array of receptors; thus, one construct could bind to CCR5 as well as other CCR receptors and another construct could bind to CXCR4 as well as a variety of other CXCR receptors. By simultaneously administering a combination of chimeric chemokine polypeptides, the greatest number of chemokine receptor types could be protected from binding by HIV or other viral isolates.

Administration and Dosing

A chimeric polypeptide of the present invention (from whatever source derived, including without limitation from recombinant and non-recombinant sources) may be used in a pharmaceutical composition when combined with a pharmaceutically acceptable carrier. Such a composition may also contain (in addition to polypeptide and a carrier) diluents, fillers, salts, buffers, stabilizers, solubilizers, and other materials well known in the art. The term "pharmaceutically acceptable" means a non-toxic material that does not interfere with the effectiveness of the biological activity of the active ingredient(s). The characteristics of the carrier will depend on the route of administration. The pharmaceutical composition of the invention may also contain cytokines, chemokines, lymphokines, or other hematopoietic factors such as M-CSF, GM-CSF, TNF, IL-1, IL-2, IL-3, IL4, IL-5, IL6, IL-7, IL-8, IL-9, IL-10, IL-11, IL-12, IL-13, IL-14, IL-15, IFN TNF0, TNF1, TNF2, G-CSF, Meg-CSF, thrombopoietin, stem cell factor, and erythropoietin. The pharmaceutical composition may further contain other agents which either enhance the activity of the polypeptide or compliment its activity or use in treatment. Such additional factors and/or agents may be included in the pharmaceutical composition to produce a synergistic effect with protein of the invention, or to minimize side effects. Conversely, polypeptides of the present invention may be included in formulations of the particular cytokine, lymphokine, other hematopoietic factor, thrombolytic or anti-thrombotic factor, or anti-inflammatory agent to minimize side effects of the cytokine, lymphokine, other hematopoietic factor, thrombolytic or anti-thrombotic factor, or anti-inflammatory agent.

A polypeptide of the present invention may be active in multimers (e.g., heterodimers or homodimers) or complexes with itself or other proteins. As a result, pharmaceutical compositions of the invention may comprise a polypeptide of the invention in such multimeric or complexed form.

The pharmaceutical composition of the invention may be in the form of a complex of the polypeptide(s) of present invention along with protein or peptide antigens. The protein and/or peptide antigen will deliver a stimulatory signal to both B and T lymphocytes. B lymphocytes will respond to antigen through their surface immunoglobulin receptor. T lymphocytes will respond to antigen through the T cell receptor (TCR) following presentation of the antigen by MHC proteins. MHC and structurally related proteins including those encoded by class I and class II MHC genes on host cells will serve to present the peptide antigen(s) to T lymphocytes. The antigen components could also be supplied as purified MHC-peptide complexes alone or with co-stimulatory molecules that can directly signal T cells. Alternatively antibodies able to bind surface immunoglobulin and other molecules on B cells as well as antibodies able to bind the TCR and other molecules on T cells can be combined with the pharmaceutical composition of the invention.

The pharmaceutical composition of the invention may be in the form of a liposome in which protein of the present invention is combined, in addition to other pharmaceutically acceptable carriers, with amphipathic agents such as lipids which exist in aggregated form as micelles, insoluble monolayers, liquid crystals, or lamellar layers in aqueous solution. Suitable lipids for liposomal formulation include, without limitation, monoglycerides, diglycerides, sulfatides, lysolecithin, phospholipids, saponin, bile acids, and the like. Preparation of such liposomal formulations is within the level of skill in the art, as disclosed, for example, in U.S. Pat. Nos. 4,235,871; 4,501,728; 4,837,028; and 4,737,323, all of which are incorporated herein by reference.

As used herein, the term "therapeutically effective amount" means the total amount of each active component of the pharmaceutical composition or method that is sufficient to show a meaningful patient benefit, i.e., treatment, healing, prevention or amelioration of the relevant medical condition, or an increase in rate of treatment, healing, prevention or amelioration of such conditions. When applied to an individual active ingredient, administered alone, the term refers to that ingredient alone. When applied to a combination, the term refers to combined amounts of the active ingredients that result in the therapeutic effect, whether administered in combination, serially or simultaneously.

In practicing the method of treatment or use of the present invention, a therapeutically effective amount of polypeptide of the present invention is administered to an organism, preferably a mammal, having a condition to be treated. Chimeric polypeptides of the present invention may be administered in accordance with the method of the invention either alone or in combination with other therapies such as treatments employing cytokines, lymphokines or other hematopoietic factors. When co-administered with one or more cytokines, lymphokines or other hematopoietic factors, polypeptides of the present invention may be administered either simultaneously with the cytokine(s), lymphokine(s), other hematopoietic factor(s), thrombolytic or anti-thrombotic factors, or sequentially. If administered sequentially, the attending physician will decide on the appropriate sequence of administering protein of the present invention in combination with cytokine(s), lymphokine(s), other hematopoietic factor(s), thrombolytic or anti-thrombotic factors.

Administration of polypeptides of the present invention used in the pharmaceutical composition or to practice the method of the present invention can be carried out in a variety of conventional ways, such as oral ingestion, inhalation, topical application or cutaneous, subcutaneous, intraperitoneal, parenteral or intravenous injection. Intravenous administration to the patient is preferred.

When a therapeutically effective amount of polypeptide of the present invention is administered orally, polypeptide of the present invention will be in the form of a tablet, capsule, powder, solution or elixir. When administered in tablet form, the pharmaceutical composition of the invention may additionally contain a solid carrier such as a gelatin or an adjuvant. The tablet, capsule, and powder contain from about 5 to 95% polypeptide of the present invention, and preferably from about 25 to 90% polypeptide of the present invention. When administered in liquid form, a liquid carrier such as water, petroleum, oils of animal or plant origin such as peanut oil, mineral oil, soybean oil, or sesame oil, or synthetic oils may be added. The liquid form of the pharmaceutical composition may further contain physiological saline solution, dextrose or other saccharide solution, or glycols such as ethylene glycol, propylene glycol or polyethylene glycol. When administered in liquid form, the pharmaceutical composition contains from about 0.5 to 90% by weight of polypeptide of the present invention, and preferably from about 1 to 50% polypeptide of the present invention.

When a therapeutically effective amount of polypeptide of the present invention is administered by intravenous, cutaneous or subcutaneous injection, polypeptide of the present invention will be in the form of a pyrogen-free, parenterally acceptable aqueous solution. The preparation of such parenterally acceptable polypeptide solutions, having due regard to pH, isotonicity, stability, and the like, is within the skill in the art. A preferred pharmaceutical composition for intravenous, cutaneous, or subcutaneous injection should contain, in addition to chimeric polypeptide of the present invention, an isotonic vehicle such as Sodium Chloride Injection, Ringer's Injection, Dextrose Injection, Dextrose and Sodium Chloride Injection, Lactated Ringer's Injection, or other vehicle as known in the art. The pharmaceutical composition of the present invention may also contain stabilizers, preservatives, buffers, antioxidants, or other additives known to those of skill in the art.

The amount of polypeptide of the present invention in the pharmaceutical composition of the present invention will depend upon the nature and severity of the condition being treated, and on the nature of prior treatments which the patient has undergone. Ultimately, the attending physician will decide the amount of chimeric polypeptide of the present invention with which to treat each individual patient. Initially, the attending physician will administer low doses of polypeptide of the present invention and observe the patient's response. Larger doses of polypeptide of the present invention may be administered until the optimal therapeutic effect is obtained for the patient, and at that point the dosage is not increased further. It is contemplated that the various pharmaceutical compositions used to practice the method of the present invention should contain about 0.01 ng to about 100 mg (preferably about 0.1 µg to about 10 mg, more preferably about 0.1 µg to about 1 mg) of polypeptide of the present invention per kg body weight.

The duration of intravenous therapy using the pharmaceutical composition of the present invention will vary, depending on the severity of the disease being treated and the condition and potential idiosyncratic response of each individual patient. It is contemplated that the duration of each application of the polypeptide of the present invention will be in the range of 12 to 24 hours of continuous intravenous administration. Ultimately the attending physician will decide on the appropriate duration of intravenous therapy using the pharmaceutical composition of the present invention.

Polypeptide of the invention may also be used to immunize animals to obtain polyclonal and monoclonal antibodies which specifically react with the chimeric polypeptide. Such antibodies may be obtained using either the entire chimeric polypeptide or fragments thereof as an immunogen, the fragments preferably comprising portions of both the chemokine and heterologous polypeptide domains. The peptide immunogens additionally may contain a cysteine residue at the carboxyl terminus, and are conjugated to a hapten such as keyhole limpet hemocyanin (KLH). Methods for synthesizing such peptides are known in the art, for example, as in R.P. Merrifield, J. Amer. Chem. Soc. 85, 2149-2154 (1963); J. L. Krstenansky, et al., FEBS Lett. 211, 10 (1987). Monoclonal antibodies binding to the polypeptide of the invention may be useful diagnostic agents for the immunodetection of the polypeptide. Neutralizing monoclonal antibodies binding to the chimeric polypeptide may also be useful therapeutics for both conditions associated with the chemokine corresponding to the chemokine domain of the chimeric polypeptide and also in the treatment of some forms of cancer where abnormal expression of that chemokine is involved. In the case of cancerous cells or leukemic cells, neutralizing monoclonal antibodies against the chimeric polypeptide may be useful in detecting and preventing the metastatic spread of the cancerous cells, which may be mediated by the chemokine corresponding to the chemokine domain of the chimeric polypeptide.

For compositions of the present invention which are useful for bone, cartilage, tendon, or ligament regeneration, the therapeutic method includes administering the composition topically, systematically, or locally as an implant or device. When administered, the therapeutic composition for use in this invention is, of course, in a pyrogen-free, physiologically acceptable form. Further, the composition may desirably be encapsulated or injected in a viscous form for delivery to the site of bone, cartilage, or tissue damage. Topical administration may be suitable for wound healing and tissue repair. Therapeutically useful agents other than a polypeptide of the invention which may also optionally be included in the composition as described above, may alternatively or additionally be administered simultaneously or sequentially with the composition in the methods of the invention. Preferably for bone and/or cartilage formation, the composition would include a matrix capable of delivering the polypeptide-containing composition to the site of bone and/or cartilage damage, providing a structure for the developing bone and cartilage and optimally capable of being resorbed into the body. Such matrices may be formed of materials presently in use for other implanted medical applications.

The choice of matrix material is based on biocompatibility, biodegradability, mechanical properties, cosmetic appearance, and interface properties. The particular application of the compositions will define the appropriate formulation. Potential matrices for the compositions may be biodegradable and chemically defined calcium sulfate, tricalciumphosphate, hydroxyapatite, polylactic acid, polyglycolic acid, and polyanhydrides. Other potential materials are biodegradable and biologically well-defined, such as bone or dermal collagen. Further matrices are comprised of pure proteins or extracellular matrix components. Other potential matrices are nonbiodegradable and chemically defined, such as sintered hydroxapatite, bioglass, aluminates, or other ceramics. Matrices may be comprised of combinations of any of the above mentioned types of material, such as polylactic acid and hydroxyapatite or collagen and tricalciumphosphate. The bioceramics may be altered in composition, such as in calcium-aluminate-phosphate and processing to alter pore size, particle size, particle shape, and biodegradability.

Presently preferred is a 50:50 (mole weight) copolymer of lactic acid and glycolic acid in the form of porous particles having diameters ranging from 150 to 800 microns. In some applications, it will be useful to utilize a sequestering agent, such as carboxymethyl cellulose or autologous blood clot, to prevent the chimeric polypeptide compositions from disassociating from the matrix.

A preferred family of sequestering agents is cellulosic materials such as alkylcelluloses (including hydroxyalkylcelluloses), including methylcellulose, ethylcellulose, hydroxyethylcellulose, hydroxypropylcellulose, hydroxypropylmethylcellulose, and carboxymethylcellulose, the most preferred being cationic salts of carboxymethylcellulose (CMC). Other preferred sequestering agents include hyaluronic acid, sodium alginate, poly(ethylene glycol), polyoxyethylene oxide, carboxyvinyl polymer and poly(vinyl alcohol). The amount of sequestering agent useful herein is 0.5-20 wt %, preferably 1-10 wt % based on total formulation weight, which represents the amount necessary to prevent desorbtion of the chimeric polypeptide from the polymer matrix and to provide appropriate handling of the composition, yet not so much that the progenitor cells are prevented from infiltrating the matrix, thereby providing the polypeptide the opportunity to assist the osteogenic activity of the progenitor cells.

In further compositions, polypeptides of the invention may be combined with other agents beneficial to the treatment of the bone and/or cartilage defect, wound, or tissue in question. These agents include various growth factors such as epidermal growth factor (EGF), platelet derived growth factor (PDGF), transforming growth factors (TGF-α and TGF-β), and insulin-like growth factor (IGF).

The therapeutic compositions are also presently valuable for veterinary applications. Particularly domestic animals and thoroughbred horses, in addition to humans, are desired patients for such treatment with polypeptides of the present invention.

The dosage regimen of a polypeptide-containing pharmaceutical composition to be used in tissue regeneration will be determined by the attending physician considering various factors which modify the action of the chimeric polypeptides, e.g., amount of tissue weight desired to be formed, the site of damage, the condition of the damaged tissue, the size of a wound, type of damaged tissue (e.g., bone), the patient's age, sex, and diet, the severity of any infection, time of administration, and other clinical factors. The dosage may vary with the type of matrix used in the reconstitution and with inclusion of other polypeptides in the pharmaceutical composition. For example, the addition of other known growth factors, such as IGF I (insulin like growth factor I), to the final composition, may also effect the dosage. Progress can be monitored by periodic assessment of tissue/bone growth and/or repair, for example, X-rays, histomorphometric determinations, and tetracycline labeling.

Polynucleotides of the present invention can also be used for gene therapy. Such polynucleotides can be introduced either in vivo or ex vivo into cells for expression in a mammalian subject. Polynucleotides of the invention may also be administered by other known methods for introduction of nucleic acid into a cell or organism (including, without limitation, in the form of viral vectors or naked DNA).

Cells may also be cultured ex vivo in the presence of chimeric polypeptides of the present invention in order to proliferate or to produce a desired effect on or activity in such cells. Treated cells can then be introduced in vivo for therapeutic purposes.

Patent and literature references cited herein are incorporated by reference as if fully set forth.

The following examples illustrate embodiments of the present invention, but are not intended to limit the scope of the disclosure.

EXAMPLE 1

Construction of Plasmids Encoding Chimeric Polypeptides

Plasmids containing chimeric gene constructions were created by ligating together four DNA fragments: a chemokine-encoding fragment, a fragment containing a linker and part of the Fc portion of the IgG4 gene, a fragment containing the rest of the Fc portion of the IgG4 gene, and a vector fragment. The resulting plasmid includes a chemokine-encoding sequence joined in-frame to a [Glycine-Serine]$_5$ linker sequence that is joined in-frame to the first codon for the hinge region-of human IgG4. The Fc region of this chimeric gene is comprised of the hinge, CH2, and CH3 regions of human IgG4, including introns, and several bases downstream from the IgG4 stop codon. The Fc portion of this chimeric gene construct also includes two amino acid changes which result in reduced Fc-receptor binding and complement fixation.

Chemokine-Encoding Fragments:

The SDF1-α fragment of clones S1-2 and S1-3 was generated using PCR with human SDF-1α cDNA as template, and with PCR primers adding NotI and BamHI sites to the upstream and downstream ends of the SDF-1α sequence, respectively. The SDF1-α fragment of clones S1-2 and S1-3 consists of eleven bases upstream of the initiating ATG of the signal sequence, through the final codon of the mature protein sequence. The DNA sequences of clones S1-2 and S1-3 appear to be identical. The SDF1-α fragment of clone SK2-2 was constructed similarly to that of S1-2 and S1-3, except that the upstream primer adding the NotI site extended through the signal sequence and into the mature protein coding sequence, with a deletion of the six nucleotides for amino acids 20 and 21 of the protein encoded by clones S1-2 and S1-3. The MIP1-α fragment of clones MP-1, MP-2, and MP-6 was generated using PCR with human MIP-1α cDNA (the HUM-CYTNEWA allele) as template, and with PCR primers adding NotI and BamHI sites to the upstream aid downstream ends of the MIP-1α sequence, respectively. The protein sequence for MIP-1α sequence is that derived from HUMCYTNEWA (SEQ ID NO:9); there is another MIP-1α allele which is not present in all humans, but HUMCYTNEWA is present in all humans. Some nucleotides were changed by the 3' MIP-1α primer in the PCR, but these nucleotide changes do not alter the amino acid sequence. The DNA sequence of MP-1 has been determined and while the DNA sequences of MP-2 and MP-6 are anticipated to be identical to that of MP-1, these clones may contain some PCR-generated DNA sequence alterations. The MIP-1α fragment of clones MP-1, MP-2, and MP-6 consists of fourteen bases upstream of the initiating ATG of the signal sequence, through the final codon of the mature protein sequence.

The MIP1-β fragment of clone MPB-X is generated using PCR with human PHA-stimulated T-cell cDNA as template, and with PCR primers adding NotI and BamHI sites to the upstream and downstream ends of the MIP-1β sequence, respectively. The nucleotide and protein sequences for MIP-1β sequence are derived from HUMACT2A (SEQ ID NO:10). The MIP-1β fragment is predicted to consist of fifteen bases upstream of the initiating ATG of the signal sequence, through the final codon of the mature protein sequence.

Linker and Partial IgG4 Fc Fragment:

All of the chimeric gene constructions use the same DNA fragment encoding a [Glycine-Serine]$_5$ linker sequence and a portion of the Fc region of human IgG4. Mutations were introduced into the IgG4 sequence, so that two amino acids in the CH2 region were changed from wild-type (in SEQ ID NO:1, 116 L has been changed to E, and 118 G has been changed to A, with corresponding nucleotide changes). The IgG4 sequence in this fragment contains an intron (nucleotides 346 to 463 in SEQ ID NO:2). The linker/partial Fc fragment was generated using PCR from the mutated human IgG4 sequence, with plasmid G081 (phhcd28.2higg4mcys) as template, and with one PCR primer adding a BamHI site and the Gly-Ser linker region to the 5' end and the other PCR primer adding a SacII site to the 3' end.

Remainder of IgG4 Fc Fragment:

This DNA fragment was generated by restriction enzyme digestion with SacII and EcoRI from the plasmid G022 encoding human IgG4 (CD28-IgG4), and purified. The IgG4 sequence in this fragment contains an intron (nucleotides 794 to 890 in SEQ ID NO:2). In the human IgG4 sequence of this fragment, a base-pair change from wild-type IgG4 sequence (in SEQ ID NO:2, base 832, C has been changed to T) was found in the intron (non-coding) region, which is expected to have no effect on expression or composition of the gene product encoded by the chimeric gene construct.

Vector Fragment:

This fragment was derived from the pED.Fc vector by digestion with NotI and EcoRI to remove the human IgG1 insert, resulting in a vector fragment with COS and CHO mammalian expression sequences that is similar to the pED vector.

EXAMPLE 2

Expression and Purification of Chimeric Polypeptides

Chimeric polypeptides S1-3, SK2-2, MP1, MP2, and MP6, encoded by chimeric plasmid constructs, were expressed by transient expression in COS cells and released into the cell culture medium. COS 1 (clone M6) cells were transiently transfected with the appropriate plasmid, using Lipofectamine™ Reagent (GibcoBRL) and following the procedure given in the product insert, with the following modifications. COS cells are seeded into 100-mm tissue culture dishes 16-24 hours prior to transfection, at about $1\text{-}1.5\times10^6$ cells per plate, in complete DME medium (DME plus 10% fetal bovine serum, 2 mM glutamine, and 100 units each penicillin and streptomycin). All incubations of COS cells were at 37 degrees C in 10% $CO_2$. For each culture dish of cells, 8 μg plasmid DNA and 48 μl Lipofectamine™ Reagent are mixed in 0.8 ml DME. After 30 minutes at room temperature, 3.2 ml DME (plus 2 mM glutamine and 100 units each penicillin and streptomycin) are added to the DNA-Lipofectamine™ Reagent mixture, mixed, and layered on top of the DME-washed COS cells. After 18 to 24 hours of incubation, this medium is replaced with complete DME medium. After an additional 2 to 4 hours incubation, the COS plates are washed twice with 5-10 ml DME, and 10 ml DME medium without serum (plus 2 mM glutamine) is added. After an additional 36 to 48 hours incubation the medium is collected, with any COS cells removed by centrifugation. The chimeric polypeptide MPB-X can also be expressed in a similar fashion.

The secreted chimeric polypeptide can be purified from this medium, or the medium can be used in various assays after quantitation of the amount of chimeric polypeptide by ELISA, using human IgG4 Kappa of known concentration to generate a standard curve.

Concentrations of the expressed chimeric polypeptides secreted into the cell culture medium were determined by ELISA using human IgG4 as a standard, and the results are shown in the table below.

TABLE 1

| Plasmid Construct: | Concentration (μg/ml): | |
|---|---|---|
| | Experiment 1: | Experiment 2: |
| S1-2 | 0.8 | not done |
| S1-3 | 1.5 | 5.0 |
| SK2-2 | 1.0 | 5.5 |

Chimeric polypeptides were purified from cell culture supernatants by immunoprecipitation using Protein A Sepharose® (Phamacia CL-4B). For example, chimeric polypeptides can be purified from 75 ml of conditioned medium by the following method. Adjust the conditioned medium to 50 mM Tris, pH 7.5. Add 100 mg Protein A Sepharose suspended in about 1 ml PBS. Incubate with rotation at 4 degrees C. overnight. Sodium azide may be added. Collect Protein A Sepharose by centrifugation, and transfer it to a BioRad Poly-Prep® column. Wash the Sepharose with 10 to 20 ml PBS. Elute the chimeric polypeptide with 12 mM HCl, and immediately neutralize the eluant by adjusting it to 50 mM Tris, pH 7.5. Elute in steps by suspending the Sepharose in 2 ml 12 mM HCl and collecting 1 ml fractions. The amount of chimeric polypeptide in the fractions can be quantitated by ELISA.

FIG. 1, panels A-D, depicts SDS-PAGE gels stained with Coomasie Blue demonstrating the expression of chimeric chemokine polypeptides in mammalian COS cells. The chimeric polypeptides were purified using protein-A, then electrophoresed on SDS-PAGE gels under reducing and non-reducing conditions. The SDF1-α-Fc chimeric polypeptides S1-3 and SK2-2 and the MIP-1α-Fc chimeric polypeptides MP-1, MP-2, and MP-6 migrated as bands with a $M_r$ of ~40 kD under reducing conditions and ~80 kD under non-reducing conditions.

EXAMPLE 3

Binding of Chimeric Polypeptides to Cells Expressing Receptors

Several human cell lines have been stained using the SDF-Fc chimeric polypeptides, demonstrating binding of the chimeric polypeptides to receptors expressed by these cells. A typical binding assay is described below. Cells were incubated on ice for a short period of time (15-60 minutes) in media containing of 2-10% FCS, 0-0.02% BSA, 0-0.02% rabbit serum, and 0.02-0.1% azide. The SDF-Fc chimeric polypeptide was added at concentrations of 0.5-2 μg/ml. After incubation with occasional mixing samples were washed with 5-6 mls of the above media. In parallel cells were stained with a mouse monoclonal antibody (12G5, IgG2a) specific for fusin/CXCR4, added at 5-20 μg/ml. For negative controls a human IgG4 or a mouse IgG2a were used at 5-20 μg/ml. The cells were then incubated for a short period of time with 100 μl of a 1:100 dilution of the second or detecting antibody. The detecting antibody used was a goat anti-human IgG F(ab')2 antibody (for the human IgG4 controls and the SDF-Fc samples) or a goat anti-mouse IgG F(ab')2 antibody (for the mouse Ig controls, murine anti-human fusin, and murine anti-human cell-surface proteins or CD3) that was labeled with PE fluorescence. After another 15-60 minutes on ice with occasional mixing followed by an extensive wash with 5-6 ml of staining media, the cells were resuspended in 400 μl and analyzed using a FACSCAN (BD) fluorescence-activated cell analyzer.

Table 2 shows the results of staining Jurkat and U937 cells by binding anti-fusin antibody or the chimeric SDF-1α chemokine polypeptides S1-3 or SK2-2 to them. Detection of fusin/CXCR4 expression by a human T cell line and a human monocyte line using a fusin-specific mAb (12G5) is comparable to detection with SDF-Fc constructs SK2-2 or S1-3. Jurkat cells, derived from a patient with acute T cell leukemia, and U937, a macrophage-like cell line derived from a patient with histiocytic lymphoma, were used. About $5\times10^5$ cells were added to 12×75 mm plastic tubes in 50 μl of staining buffer consisting of RPMI-1640 (phenol red free with 10 mM HEPES) or PBS containing 2% FCS, 2% rabbit serum, and 0.1% azide. Anti-fusin staining controls consisted of either media only or a mouse IgG2a control antibody and were equivalent in staining. The anti-fusin mAb 12G5 was added at a final concentration of 16 μg/ml (Exp. 1) or 20 μg/ml (Exp. 2) diluted in staining buffer. After 30 minutes on ice with mixing the cells were washed with 5 ml of staining buffer and 100 μl of a 1:100 dilution of Goat anti-mouse Ig PE (Southern Biotech) was added to detect cell-bound mouse antibody. For SDF-Fc staining the control consisted of either media only or human IgG4 antibody. The SDF-Fc constructs were added at a final concentration of 0.5 µg/ml for the SK2-2 in Exp. 1 or at 1 µg/ml for the S1-3 in Exp. 2. After 30 minutes on ice with mixing the cells were washed with 5 ml of staining buffer and 100 µl of a 1:100 dilution of goat anti-human Ig PE was added to detect cell-bound SDF-Fc. The control antibodies gave no increase over the second antibody only. The staining with anti-fusin (12G5) was equivalent to that seen with the SDF-Fc constructs, indicating that all human cells that were expressing the fusin receptor, as shown by anti-fusin antibody binding, also bound the SDF-Fc chimeric polypeptides. Human RPMI 8866 cells that do not express fusin (as indicated by absence of staining) did not bind SDF-Fc chimeric polypeptides (data not shown).

The data shown for Exp. 1 in Table 2 corresponds to the results shown graphically as histograms in FIG. 2. The x axis of the histograms (see FIG. 2A) was divided into three regions: M1=channel 1-11; M2=channel 11-123; and M3=channel 123-1370. The data is expressed as the percentage of appropriately gated cells in each of these regions. Also given in Table 2 is the peak channel and the median channel. The peak channel is the channel containing the highest distribution of cells. The median is the channel where 50% of the cells are to the right or left of this point. FIG. 2, panels A-D represent the histograms for Exp. 1 comparing the anti-fusin antibody 12G5 to the chimeric polypeptide SK2-2. The thinner line is that for the control while the thicker line is that for the 12G5 (FIGS. 2A and 2C) or for SK2-2 (FIGS. 2B and 2D). FIGS. 2A and 2B indicate staining of Jurkat cells. FIGS. 2C and 2D indicate staining of U937 cells.

TABLE 2

Jurkat and U937 cell staining by anti-Fusin mAb and SDF-Fc constructs

| | % of Cells in Each Channel Range | | | | |
|---|---|---|---|---|---|
| Channel Range: | M1 1-11 | M2 11-123 | M3 123-1370 | Peak Channel | Median Channel |
| Exp. 1 | | | | | |
| Jurkat Control | 97.5% | 2.5% | 0% | 3 | 3 |
| Jurkat anti-Fusin | 0.5% | 21.4% | 78.2% | 281 | 225 |
| Jurkat Control | 98.1% | 1.9% | 0% | 3 | 3 |
| Jurkat SK2-2 | 2.4% | 42.3% | 56.1% | 145 | 132 |
| U937 Control | 97.8% | 2.2% | 0% | 3 | 3 |
| U937 anti-Fusin | 0.3% | 71.8% | 28.4% | 81 | 95 |
| U937 Control | 99.6% | 0.5% | 0% | 3 | 3 |
| U937 SK2-2 | 2.3% | 72.6% | 25.5% | 47 | 63 |
| Exp. 2 | | | | | |
| Jurkat Control | 91.6% | 8.5% | 0.1% | 5 | 5 |
| Jurkat anti-Fusin | 0.4% | 48.1% | 51.9% | 121 | 134 |
| Jurkat Control | 86.3% | 13.9% | 0% | 6 | 6 |
| Jurkat S1-3 | 6.5% | 51.3% | 42.8% | 139 | 106 |
| U937 Control | 98.9% | 1.1% | 0% | 4 | 4 |
| U937 anti-Fusin | 0.2% | 53% | 47.5% | 114 | 118 |
| U937 Control | 98% | 2.0% | 0% | 5 | 5 |
| U937 S1-3 | 1.0% | 77.3% | 22.1% | 62 | 78 |

TABLE 3

Lymphocyte and dendritic cell staining by anti-Fusin mAb and SDF-Fc constructs

| | % of Cells in Each Channel Range | | | | |
|---|---|---|---|---|---|
| Channel Range: | M1 1-11 | M2 11-123 | M3 123-1370 | Peak Channel | Median Channel |
| T lymphocytes | | | | | |
| Control * | 74.8% | 2.3% | 0% | 1 | 2 |
| anti-CD3 | 2.8% | 4.2% | 88.7% | 610 | 523 |
| anti-Fusin | 39.3% | 56.9% | 3.2% | 1 | 18 |
| IgG4 Control ** | 79.8% | 1.8% | 0.2% | 1 | 2 |
| SDF-Fc SK2-2 | 27.2% | 70.5% | 2.5% | 37 | 21 |
| SDF-Fc S1-2 | 31.5% | 66.4% | 2.3% | 31 | 20 |
| Dendritic Cells and other Adherent Cells | | | | | |
| Control * | 38.6% | 60.5% | 1.5% | 13 | 13 |
| anti-Fusin | 16.1% | 59.0% | 25.1% | 12 | 31 |
| IgG4 Control | 53.1% | 47.3% | 0.1% | 8 | 11 |
| SDF-Fc SK2-2 | 18.6% | 77.6% | 4.3% | 10 | 23 |

* Mouse gamma 2a control + Goat anti-Mouse PE second step
** Human IgG4 control + Goat anti-Human PE second step Table 3 shows the results of staining T lymphocytes isolated from peripheral blood, and dendritic and other adherent cells isolated from human bone marrow (following culture in media containing IL-4 and GMSF then TNF), by binding anti-fusin antibody or the chimeric SDF-1 α chemokine polypeptides S1-3 to them. These results indicate that a variety of cells expressing the fusin receptor bind the chimeric SDF-1 α chemokine polypeptides.

TABLE 4

Effect of adding Human SDF-1β during staining of U937 cells by Anti-Fusin mAb and chimeric SDF-Fc constructs

| | % of Cells in Each Channel Range | | | | |
|---|---|---|---|---|---|
| Channel Range: | M1 1-11 | M2 11-123 | M3 123-1370 | Peak Channel | Median Channel |
| Control * | 93.5% | 5.7% | 0.8% | 3 | 3 |
| anti-Fusin | 0% | 41.3% | 58.8% | 157 | 136 |
| 50 ng/ml Human SDF-1β + anti-Fusin | 0% | 47.1% | 52.9% | 106 | 127 |
| 500 ng/ml Human SDF-1β + anti-Fusin | 0% | 70.0% | 30.0% | 95 | 95 |
| IgG4 Control ** | 99.0% | 1.0% | 0% | 3 | 3 |
| SDF-Fc SK2-2 | 2.0% | 97.0% | 1.5% | 47 | 47 |
| 50 ng/ml Human SDF-1β + SDF-Fc SK2-2 | 1.6% | 97% | 1.6% | 45 | 46 |
| 500 ng/ml Human SDF-1β + SDF-Fc SK2-2 | 8.4% | 91.1% | 0.7% | 29 | 30 |
| SDF-Fc S1-3 | 1.4% | 96.7% | 1.9% | 48 | 47 |
| 50 ng/ml Human SDF-1β + SDF-Fc S1-2 | 2.0% | 96.7% | 1.9% | 42 | 46 |
| 500 ng/ml Human SDF-1β + SDF-Fc S1-2 | 11.0% | 88.7% | 0.3% | 30 | 26 |

* Mouse gamma 2a control + Goat anti-Mouse PE second step
** Human IgG4 control + Goat anti-Human PE second step For the experiment shown in Table 4, purified human SDF-1β chemokine, prepared in E. coli and containing an N-terminal methionine residue, was mixed with either anti-fusin antibody or chimeric SDF-1α polypeptide, then incubated with cells on ice in the presence of azide. The results shown in Table 4 indicate that a 10-fold increase in the amount of SDF-1β chemokine eliminates some anti-fusin antibody binding to cells. but does not reduce the amount of chimeric SDF-Fc polypeptide binding to cells. This suggests that the affinity of the chimeric SDF-Fc polypeptide for its binding site on cells. presumably the fusin receptor, is sufficiently high that it cannot be competed off by addition of excess SDF-1β chemokine.

Binding of the MIP-1α-Fc and MIP-1β-Fc chimeric polypeptides to cells is determined by a cell-staining assay analogous to that described above.

EXAMPLE 4

Alteration or Inhibition of Calcium Flux by Chimeric Polypeptides

When chemokines bind to receptors present within the membranes of cells, a calcium flux may be induced. When chimeric chemokine polypeptides bind to these receptors, the duration, intensity, or other properties of the calcium flux may be altered, or the calcium flux may be inhibited. This calcium flux may be measured using the following protocol, and the effects of chemokine and chimeric chemokine polypeptide binding to receptors compared.

Harvest the cells, wash twice in first wash buffer (10 mM MOPS or HEPES at about pH7.2, 1 mM $CaCl_2$, 1 mM glucose, 140 mM NaCl), adjust to $10^7$ cells per ml, resuspend in loading/FACS buffer (10 mM MOPS or HEPES at about pH7.2, 1 mM $CaCl_2$, 1 mM glucose, 140 mM NaCl, 0.2% BSA). Dissolve 50 μg vial of FLUO-3 ester (Molecular Probes, cat. #F-1242) in 50 μl DMSO right before use. Add 5 μl FLUO-3 ester (approximately 5 μM, different concentrations may be needed for different cell types) for each ml of cells. Incubate for 20-30 minutes at room temperature. Wash twice in medium (for example, RPMI with fetal calf serum). Resuspend cells at $10^7$ per ml in medium (or loading/FACS buffer). Store on ice until ready to use (or store at room temperature). To test for calcium flux, dilute cells into loading/FACS buffer, 100 μl of cells per 1 ml buffer. Using a FACSCAN (BD) fluorescence-activated cell analyzer, determine the background reading for the loaded cells (use FL1 channel; set maximum signal at about 200). Stimulate appropriately (with one or more reagents, sequentially) and read on FACS for 3-15 minutes or more, watching for an increase in fluorescence due to calcium flux. The ionophore ionomycin can be used as a positive control to demonstrate that the cells being tested are capable of demonstrating a calcium flux.

EXAMPLE 5

Stimulation of Chemotaxis by Chimeric Polypeptides

Chimeric chemokine polypeptides can be tested for their ability to stimulate chemotaxis by any of the following assays for chemotactic activity. These assays (which will identify proteins that induce or prevent chemotaxis) measure the ability of a protein to induce the migration of cells across a membrane as well as the ability of a protein to induce the adhesion of one cell population to another cell population. Suitable assays for movement and adhesion include, without limitation, those described in: Current Protocols in Immunology, Ed. by J. E. Coligan, A. M. Kruisbeek, D. H. Margulies, E. M. Shevach, W. Strober, Pub. by Greene Publishing Associates and Wiley-Interscience (Chapter 6.12, Measurement of alpha and beta Chemokines 6.12.1-6.12.28); Taub et al., J. Clin. Invest. 95:1370-1376, 1995; Lind et al., APMIS 103: 140-146, 1995; Muller et al., Eur. J. Immunol. 25: 1744-1748; Gruber et al., J. of Immunol. 152:5860-5867, 1994; Johnston et al., J. of Immunol. 153: 1762-1768, 1994; all of which are incorporated herein by reference.

EXAMPLE 6

Down Modulation of Receptor by Chimeric Polypeptide Binding

The ability of the chimeric SDF-Fc polypeptides to down-modulate chemokine receptors was compared with that of human SDF-1β. Jurkat cells were incubated for 3 hours or 15 hours at 37 degrees C. with either human SDF-1β or chimeric SDF-Fc polypeptide, followed by a wash of the cells and staining with anti-fusin antibody as described in Example 3. Mock experiments involved incubating cells with COS cell supernatant containing neither SDF-1β nor chimeric SDF-Fc polypeptide. The results of these experiments are shown in Table 5.

TABLE 5

Down-Modulation of Fusin/CXCR4 by Incubation with Human SDF-1β or chimeric SDF-FC

| | % of Cells in Each Channel Range | | | | |
|---|---|---|---|---|---|
| Channel Range: | M1<br>1-11 | M2<br>11-123 | M3<br>123-1370 | Peak<br>Channel | Median<br>Channel |
| Jurkat 3-hour Incubation | | | | | |
| Media control | 97.5% | 2.5% | 0% | 3 | 3 |
| Anti-fusin Media | 0.4% | 20.2% | 79.6% | 281 | 231 |
| 500 ng/ml Human SDF1β | 14.1% | 83.2% | 3.1% | 20 | 22.3 |
| Mock | 0.4% | 12.3% | 87.2% | 276 | 302 |
| 70 ng/ml SDF-Fc S1-2 | 6.1% | 91.7% | 2.5% | 23 | 26 |
| 140 ng/ml SDF-Fc S1-3 | 15.5% | 82.5% | 2.4% | 13 | 20 |
| 90 ng/ml SDF-Fc SK2-2 | 11.3% | 86.8% | 2.4% | 23 | 22 |
| Jurkat 15-hour Incubation | | | | | |
| Media control | 97.5% | 2.5% | 0% | 3 | 3 |
| Anti-fusin Media | 0.4% | 20.2% | 79.6% | 281 | 231 |
| 500 ng/ml Human SDF1β | 1.7% | 77.7% | 20.9% | 66 | 75 |
| 70 ng/ml SDF-FC S-2 | 5.9% | 91.7% | 2.7% | 35 | 34 |
| 140 ng/ml SDF-FC S1-3 | 9.2% | 90.0% | 1.1% | 26 | 25 |
| 90 ng/ml SDF-FC SK2-2 | 7.0% | 91.7% | 1.5% | 38 | 28 |

The apparent down-modulation of fusin receptor by human SDF-1β is not simply due to blocking of staining by the anti-fusin antibody by the binding of SDF-1β to fusin, since the results shown in Table 4 above indicate that the presence of human SDF-1β does not prevent anti-fusin binding to the extent observed here. The down-modulation by the chimeric SDF-Fc polypeptide is demonstrated by the failure of anti-fusin antibody to bind after incubation with this chimeric polypeptide (Table 5) and the weak staining of these cells with PE-labeled goat anti-human Ig to detect chimeric SDF-Fc polypeptide remaining after the 3- or 15-hour incubation (data not shown).

Down-regulation-of receptor by binding of MIP-1α-Fc and MIP-1β-Fc chimeric polypeptides to cells is determined by an assay for receptor down-regulation analogous to that described above.

What is claimed is:

1. A composition comprising a chimeric polypeptide, the chimeric polypeptide comprising at least one chemokine polypeptide covalently attached to at least one heterologous polypeptide, wherein the heterologous polypeptide is an Fc polypeptide, wherein the chemokine polypeptide comprises SEQ ID NO:1 from amino acid 22 to amino acid 328.

2. The composition of claim 1, wherein the chemokines polypeptide comprises the amino acid sequence selected from the group consisting of
    (a) SEQ ID NO:1
    (b) SEQ ID NO:1 from amino acid 20 to amino acid 328
    (c) SEQ ID NO:1 from amino acid 21 to amino acid 328
    (d) SEQ ID NO:3.

3. The composition of claim 2 wherein the chimeric polypeptide comprises the amino acid sequence selected from the group consisting of:
    (a) the amino acid sequence of SEQ ID NO:1;
    (b) the amino acid sequence of SEQ ID NO:1 from amino acid 20 to amino acid 328; and
    (c) the amino acid sequence of SEQ ID NO:1 from amino acid 22 to amino acid 328.

4. The composition of claim 2 wherein the chemokine polypeptide comprises
the amino acid sequence of SEQ ID NO:53.

5. The composition of claim 2 wherein the chemokine polypeptide comprises the amino acid sequence of SEQ ID NO:1.

6. The composition of claim 2 wherein the chemokine polypeptide comprises the amino acid sequence of SEQ ID NO:3.

7. The composition of claim 2, further comprising a pharmaceutically acceptable carrier.

8. The composition of claim 2 wherein the chemokine polypeptide comprises SEQ ID NO:1 from amino acid 20 to amino acid 328.

9. The composition of claim 2 wherein the chemokine polypeptide comprises SEQ ID NO:1 from amino acid 20 to amino acid 328.

10. The composition of claim 2 wherein the chemokine polypeptide comprises SEQ ID NO:1 from amino acid 22 to amino acid 328.

11. The composition of claim 2 wherein the chemokine polypeptide consists of SEQ ID NO:3 from amino acid 20 to amino acid 326.

12. A chimeric polypeptide produced according to a process comprising:
    (a) growing a culture of a host cell in a suitable culture medium, wherein the host cell has been transformed with a polynucleotide comprising at least one expression control sequence, wherein the polynucleotide encodes a chimeric polypeptide, the chimeric polypeptide comprising at least one chemokine polypeptide covalently attached to at least one heterologous polypeptide, wherein the heterologous polypeptide is an Fc polypeptide and the chemokine polypeptide comprises SEQ ID NO:1 from amino acid 22 to amino acid 328, and (b) purifying said chimeric polypeptide from the culture.

13. The polypeptide of claim 12 wherein the chemokine polypeptide comprises SEQ ID NO:1.

14. The polypeptide of claim 12 wherein the chemokine polypeptide comprises SEQ ID NO:1 from amino acid 20 to amino acid 328.

15. The polypeptide of claim 12 wherein the chemokine polypeptide comprises SEQ ID NO:1 from amino acid 21 to amino acid 328.

16. The polypeptide of claim 12 wherein the chemokine polypeptide comprises SEQ ID NO:1 from amino acid 22 to amino acid 328.

17. The polypeptide of claim 12 wherein the chemokine polypeptide comprises SEQ ID NO:3.

18. The polypeptide of claim 12 wherein the chemokine polypeptide consists of SEQ ID NO:3 from amino acid 20 to amino acid 326.

* * * * *